(12) United States Patent
Ehteshami et al.

(10) Patent No.: US 12,257,160 B2
(45) Date of Patent: Mar. 25, 2025

(54) INTERVERTEBRAL SPACER

(71) Applicant: ADDITIVE IMPLANTS, INC., Phoenix, AZ (US)

(72) Inventors: John R. Ehteshami, Paradise Valley, AZ (US); Mahyar Zoghi, Phoenix, AZ (US)

(73) Assignee: ADDITIVE IMPLANTS, INC., Phoenix, AZ (US)

( * ) Notice: Subject to any disclaimer, the term of this patent is extended or adjusted under 35 U.S.C. 154(b) by 390 days.

(21) Appl. No.: 17/763,599

(22) PCT Filed: Sep. 24, 2020

(86) PCT No.: PCT/US2020/052412
§ 371 (c)(1),
(2) Date: Mar. 24, 2022

(87) PCT Pub. No.: WO2021/061928
PCT Pub. Date: Apr. 1, 2021

(65) Prior Publication Data
US 2022/0331123 A1    Oct. 20, 2022

Related U.S. Application Data

(63) Continuation of application No. 17/030,191, filed on Sep. 23, 2020, now Pat. No. 11,123,201.

(60) Provisional application No. 62/905,011, filed on Sep. 24, 2019.

(51) Int. Cl.
A61F 2/44    (2006.01)
A61F 2/30    (2006.01)

(52) U.S. Cl.
CPC .... *A61F 2/447* (2013.01); *A61F 2002/30507* (2013.01); *A61F 2002/30622* (2013.01); *A61F 2002/30784* (2013.01); *A61F 2002/30841* (2013.01); *A61F 2002/3092* (2013.01); *A61F 2002/3093* (2013.01); *A61F 2002/30968* (2013.01); *A61F 2/442* (2013.01); *A61F 2/4455* (2013.01)

(58) Field of Classification Search
None
See application file for complete search history.

(56) References Cited

U.S. PATENT DOCUMENTS

| | | |
|---|---|---|
| 5,609,635 A | 3/1997 | Michelson |
| 6,395,035 B2 | 5/2002 | Bresina et al. |
| 6,592,624 B1 | 7/2003 | Fraser |
| 6,723,126 B1 | 4/2004 | Berry |
| 6,979,353 B2 | 12/2005 | Bresina |
| 7,238,203 B2 | 7/2007 | Bagga et al. |
| 7,867,277 B1 | 1/2011 | Tohmeh |
| 7,918,891 B1 | 4/2011 | Curran |
| 8,328,872 B2 | 12/2012 | Duffield et al. |

(Continued)

*Primary Examiner* — Tessa M Matthews
(74) *Attorney, Agent, or Firm* — David Meibos; Maywood IP Law

(57) ABSTRACT

Intervertebral implant systems include spacers that may have solid and porous bodies integrally formed together as a single part. The bone-facing sides of the spacers include asymmetric lobes which may include solid and/or porous portions. Bone anchor holes may extend through the spacers and lobes, to receive bone anchors. A helically fluted bone anchor may be received in the bone anchor holes.

12 Claims, 16 Drawing Sheets

(56) References Cited

U.S. PATENT DOCUMENTS

| | | |
|---|---|---|
| 9,885,150 B2 * | 2/2018 | Mennucci ................ B30B 5/04 |
| 10,299,938 B1 | 5/2019 | Ehteshami |
| 2003/0040802 A1 | 2/2003 | Errico |
| 2010/0057206 A1 | 3/2010 | Duffield et al. |
| 2010/0076557 A1 | 3/2010 | Miller |
| 2010/0298941 A1 | 11/2010 | Hes et al. |
| 2010/0331982 A1 | 12/2010 | McCombe |
| 2011/0071635 A1 | 3/2011 | Zhang et al. |
| 2011/0082551 A1 | 4/2011 | Kraus |
| 2011/0313532 A1 | 12/2011 | Hunt |
| 2012/0095559 A1 | 4/2012 | Woods et al. |
| 2013/0023992 A1 | 1/2013 | Moskowitz |
| 2013/0131806 A1 | 5/2013 | Carpenter |
| 2014/0088711 A1 | 3/2014 | Chin et al. |
| 2014/0277456 A1 * | 9/2014 | Kirschman ............. A61F 2/447 |
| | | 623/17.11 |
| 2017/0340453 A1 | 11/2017 | Kaufmann et al. |
| 2017/0348114 A1 | 12/2017 | Jones et al. |
| 2018/0325694 A1 | 11/2018 | Petersheim et al. |
| 2019/0083270 A1 | 3/2019 | Milz et al. |
| 2019/0133783 A1 | 5/2019 | Unger et al. |
| 2019/0343652 A1 * | 11/2019 | Petersheim ........... A61F 2/4611 |
| 2020/0078188 A1 | 3/2020 | Ehteshami |
| 2020/0078189 A1 | 3/2020 | Ehteshami |
| 2020/0078191 A1 | 3/2020 | Ehteshami et al. |
| 2020/0197050 A1 | 6/2020 | Ehteshami |
| 2022/0409388 A1 * | 12/2022 | Barfield ................ A61F 2/4455 |
| 2023/0355396 A1 * | 11/2023 | Perryman ........... A61F 2/30771 |

\* cited by examiner

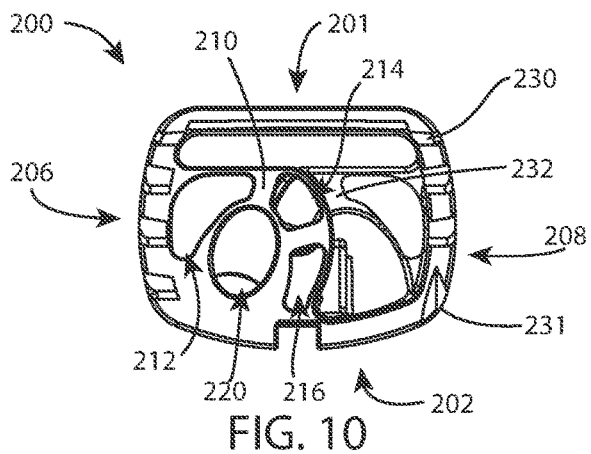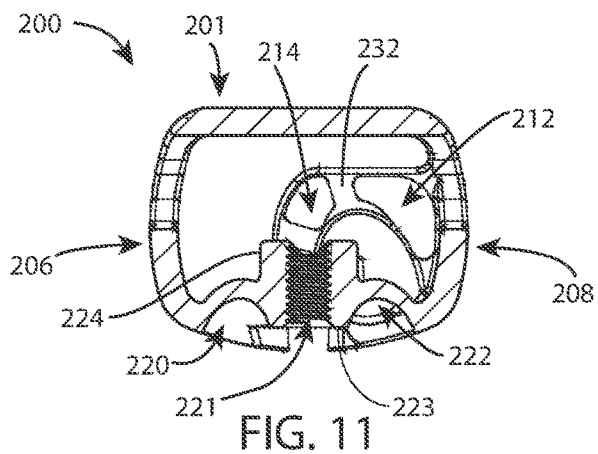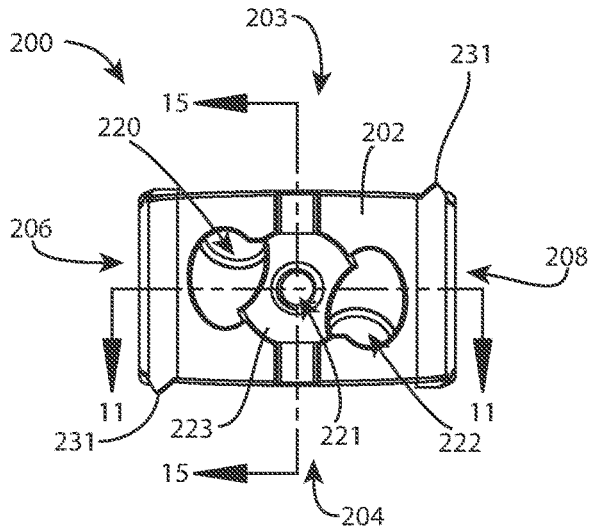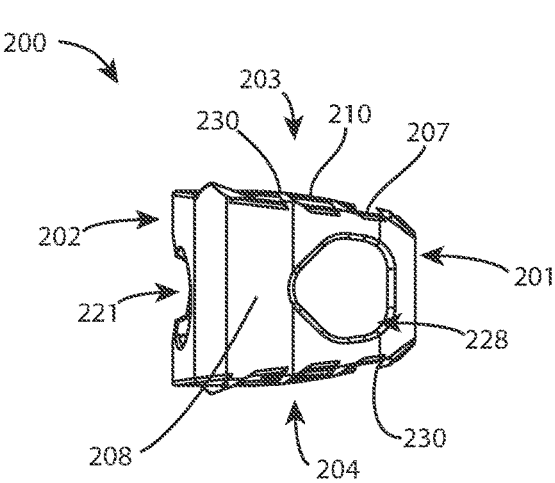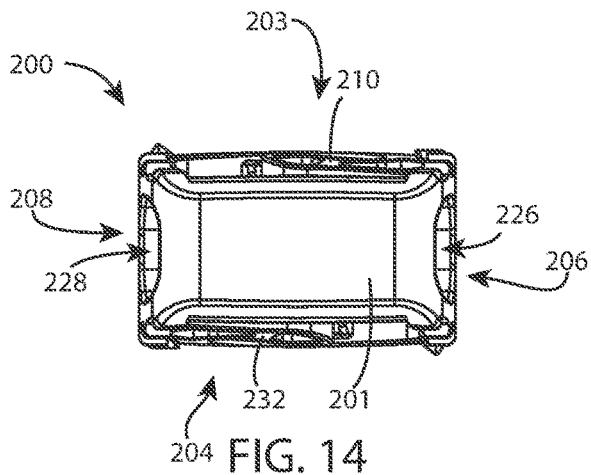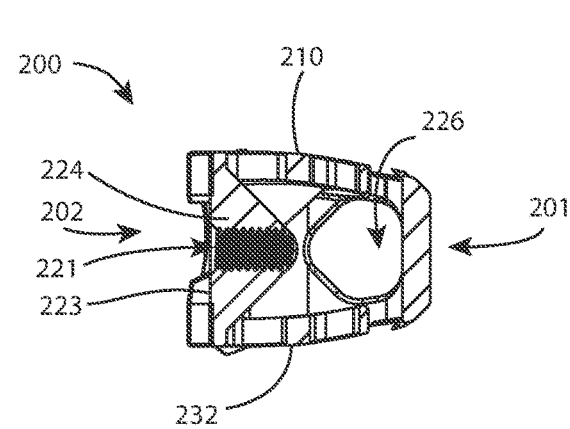

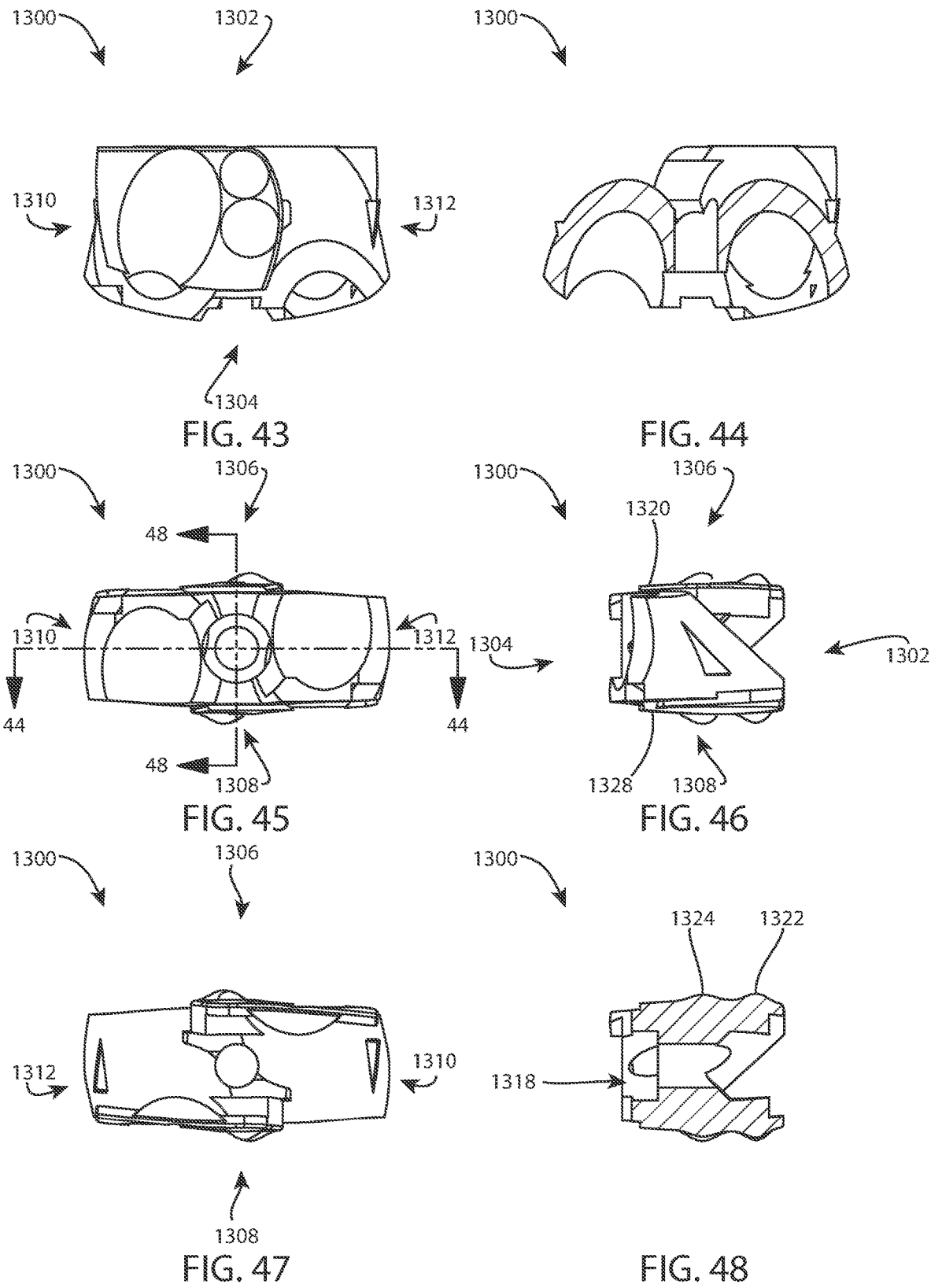

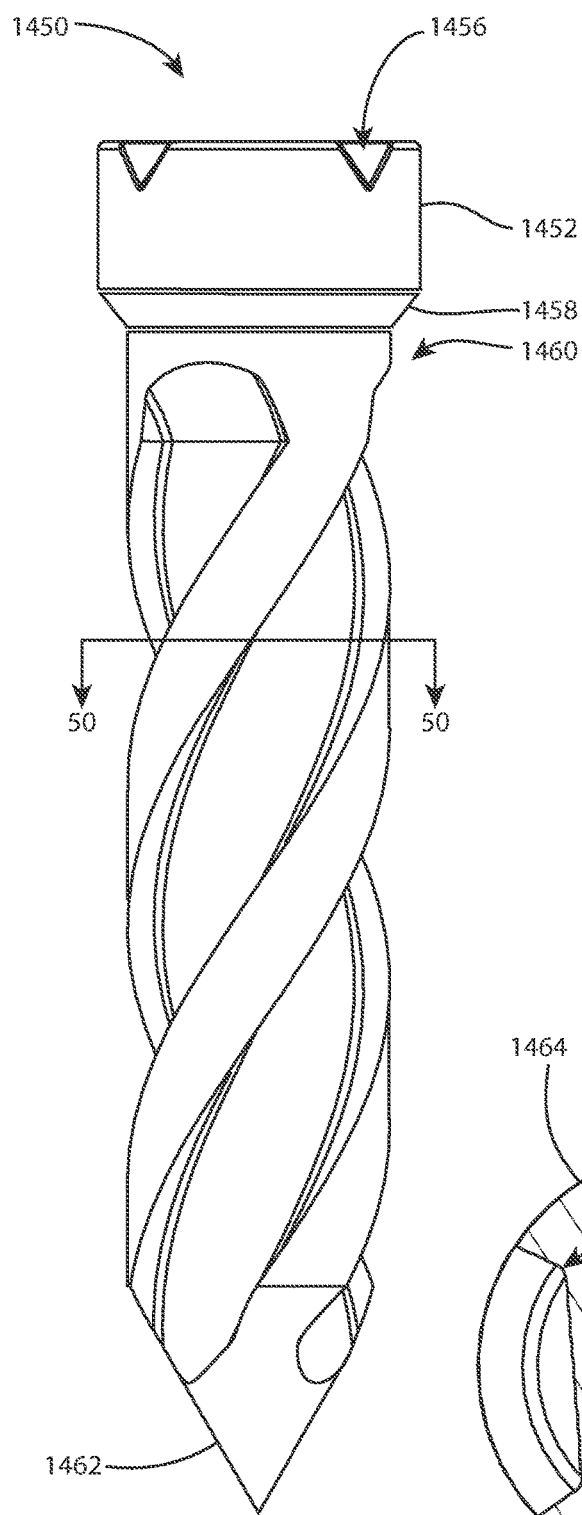
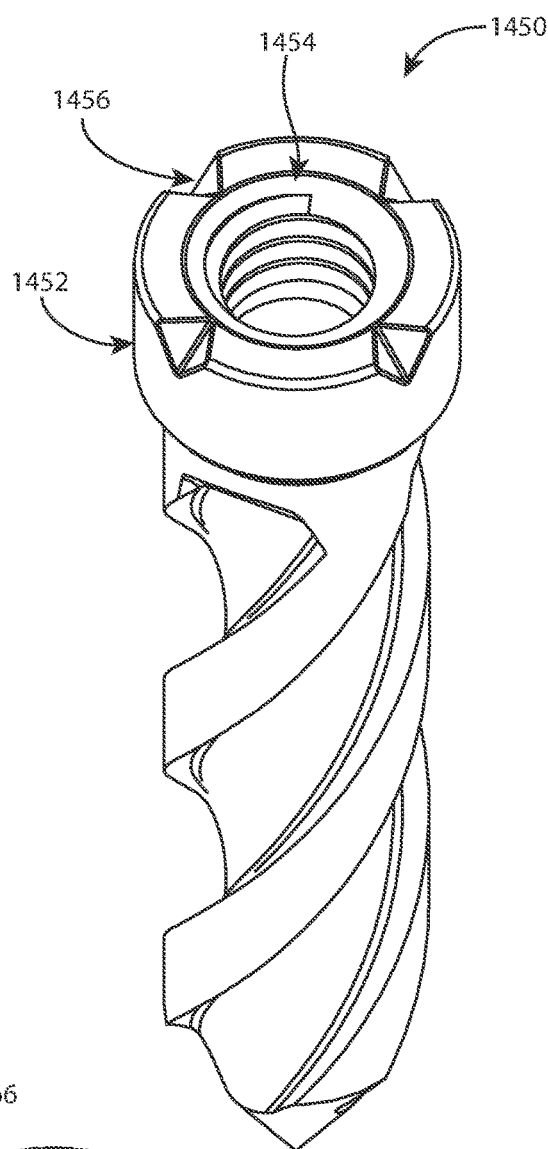
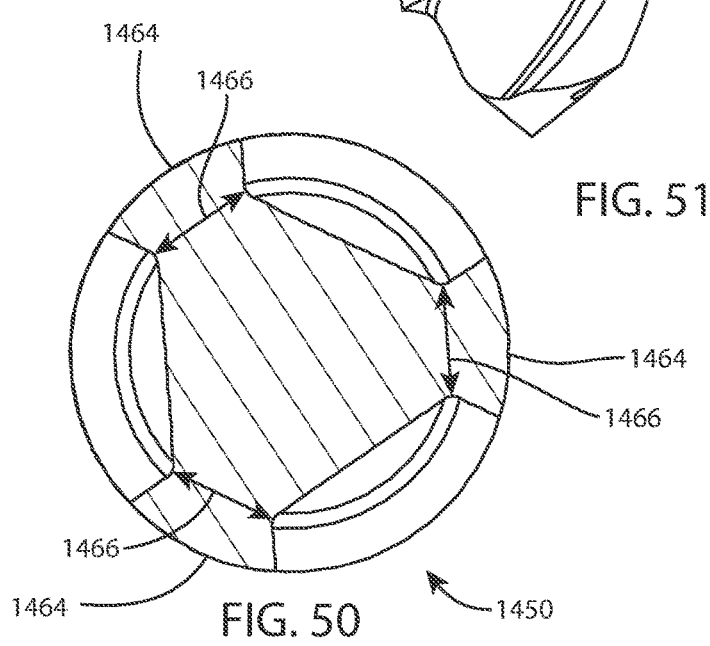
FIG. 49
FIG. 50
FIG. 51

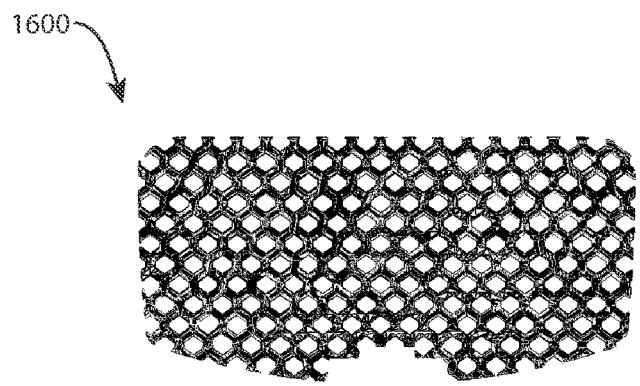
FIG. 55A
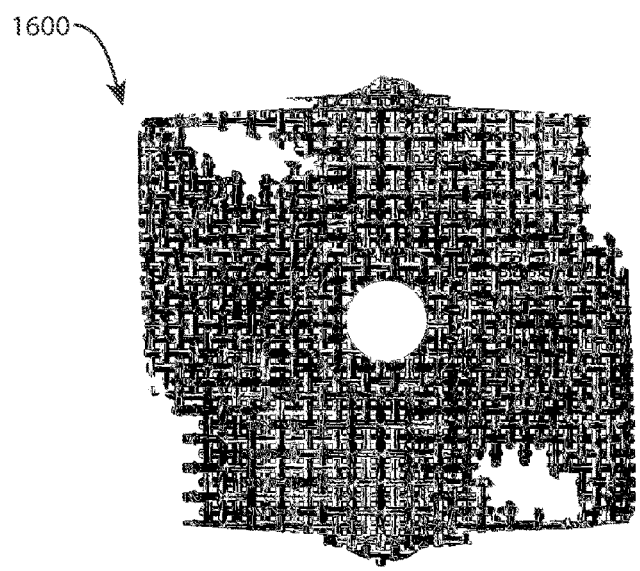
FIG. 56A
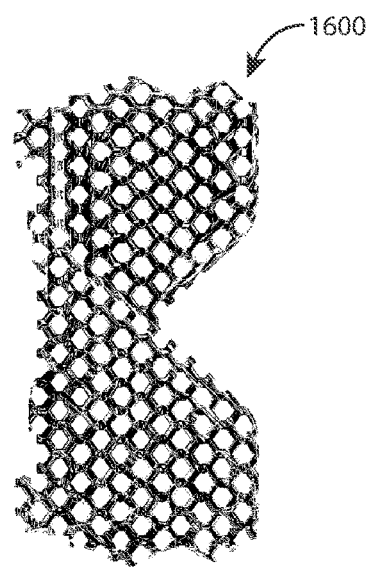
FIG. 57A
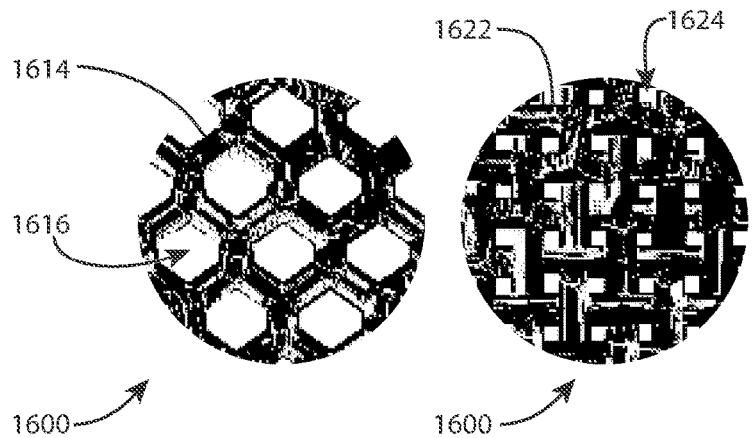
FIG. 55B
FIG. 56B
FIG. 57B

INTERVERTEBRAL SPACER

CROSS-REFERENCE TO RELATED APPLICATIONS

This application is a U.S. national stage filing under 35 U.S.C. § 371 of International Application No. PCT/US2020/052412, filed on Sep. 24, 2020, which claims the benefit of U.S. Provisional Application No. 62/905,011, filed on Sep. 24, 2019. International Application No. PCT/US2020/052412 is also a continuation of U.S. patent application Ser. No. 17/030,191 filed on Sep. 23, 2020 which issued on Sep. 21, 2021 as U.S. Pat. No. 11,123,201. All of the foregoing are incorporated as though set forth herein in their entirety.

TECHNICAL FIELD

The present disclosure relates to an intervertebral spacer. More specifically, the present disclosure relates to a cervical intervertebral spacer with a solid body, a porous body, bone screws, and a locking screw.

BACKGROUND

Intervertebral spacers are designed to fuse adjacent superior and inferior vertebrae. Over time, the vertebrae and bone graft contained in the intervertebral spacer heal together to form a unitary fusion mass for long term stability and load bearing.

One of the design objectives for an intervertebral spacer is to provide adequate area for the bone graft to contact the adjacent superior and inferior vertebral endplates so that the resulting fusion mass is strong enough to withstand long-term loads.

Another design objective is to provide initial fixation of the intervertebral spacer to the vertebral bodies so that the bone/bone graft interface is stable enough to promote healing and development of the fusion mass. One way to achieve initial fixation is to insert bone screws through the intervertebral spacer and into the adjacent vertebral endplates. The initial fixation must be strong enough to withstand initial loads and therefore the intervertebral spacer and bone screws must include adequate material, for example at the spacer/screw interface.

The anatomical dimensions of the cervical spine tend to cause conflict between these two design objectives because the overall space available for the implant is limited by the size of the cervical disc space and vertebral bodies. Increasing bone graft area at the superior and inferior endplates of the intervertebral spacer tends to weaken the spacer. Increasing material in the intervertebral spacer (for example around the screw) tends to decrease the available bone graft area.

Thus, there is a need for an intervertebral spacer that provides adequate bone graft area and sufficient strength for initial stability.

Intervertebral spacers may be fabricated by additive manufacturing technologies. Additive manufacturing operations have the capability to fabricate individual parts having different zones of material density, for example a substantially fully dense structural zone associated with one or more zones of porous material. Additive manufacturing operations are also compatible with certain design features that are challenging or impossible to fabricate by conventional operations such as turning, milling, welding, and the like.

Unsupported features may require special treatment in order to have a successful outcome via additive manufacturing. For example, unsupported features may have to be connected to temporary support structures to hold such features in place during a build. Temporary support structures may be removed in a subsequent operation after the additive manufacturing operation by breaking, grinding, or otherwise eliminating the support structures. While support structures may ensure a satisfactory outcome for the additive manufacturing operation, their removal may be difficult in small parts with limited access to interior cavities that contain the support structures.

Thus, there is a need for an intervertebral spacer that includes different zones of material density, wherein at least some of the less dense material supports overhangs, undercuts, and similar features in at least one zone of substantially fully dense material.

SUMMARY

The various systems and methods of the present technology have been developed in response to the present state of the art, and in particular, in response to the problems and needs in the art that have not yet been fully solved by currently available intervertebral spacers. The systems and methods of the present technology may provide adequate area for bone graft; sufficient strength for initial stability; different zones of implant material density, including at least some less dense material that supports at least some fully dense material; and net-shape fabrication by additive manufacturing, without relying upon temporary support structures.

To achieve the foregoing, and in accordance with the technology as embodied and broadly described herein, in an aspect of the technology an intervertebral implant system includes: an intervertebral spacer including a solid body and a porous body integrally formed together as a single part, wherein the intervertebral spacer includes a leading side, an opposite trailing side, a first side, an opposite second side, a right side, an opposite left side, a perimeter wall, a first lobe, and a bone anchor hole; wherein the perimeter wall extends around the leading, trailing, right, and left sides between the first and second sides, wherein the first lobe extends from the perimeter wall across a portion of the first side toward a central region of the first side, wherein the bone anchor hole extends through the first lobe so that the first lobe surrounds the bone anchor hole; and a bone anchor configured to be received in the bone anchor hole so that a portion of the bone anchor protrudes outwardly from the first side.

Embodiments of this aspect of the technology may include one or more of the following attributes. The solid body includes the perimeter wall, wherein the perimeter wall surrounds the porous body and abuts a perimeter portion of the porous body. The porous body supports at least a portion of the perimeter wall during fabrication of the intervertebral spacer. The first lobe is elevated outwardly relative to the perimeter wall at the first side. The solid body includes a first solid portion of the first lobe and the porous body includes a first porous portion of the first lobe. The first porous portion of the first lobe is elevated outwardly relative to the first solid portion of the first lobe and the perimeter wall at the first side. The bone anchor hole extends obliquely through the perimeter wall and the first lobe. The solid body includes a wall extending obliquely between the perimeter wall and the first lobe, and surrounding the bone anchor hole. The system includes: a locking mechanism; wherein the bone anchor includes a head, wherein the head includes a notch; wherein when the bone anchor is received in the bone anchor hole, the notch engages the locking mechanism to prevent the bone anchor from backing out of the bone anchor hole.

In another aspect of the technology an intervertebral implant system includes: an intervertebral spacer including a leading side, a trailing side opposite the leading side, a first bone-facing side, a second bone-facing side opposite the first bone-facing side, a right side, a left side opposite the right side, a perimeter wall, a first lobe, and a bone anchor hole; wherein the perimeter wall extends around the leading side, trailing side, right side, and left side between the first and second bone-facing sides; wherein the first lobe extends from the perimeter wall across a portion of the first bone-facing side toward a central region of the first bone-facing side; wherein the bone anchor hole extends obliquely through the perimeter wall and the first lobe so that the first lobe surrounds the bone anchor hole; and a bone anchor configured to be received in the bone anchor hole so that a portion of the bone anchor protrudes outwardly from the first bone-facing side.

Embodiments of this aspect of the technology may include one or more of the following attributes. The intervertebral spacer includes a solid body and a porous body integrally formed together as a single part, wherein the solid body includes the perimeter wall, wherein the perimeter wall surrounds the porous body and abuts a perimeter portion of the porous body. The porous body supports at least a portion of the perimeter wall during fabrication of the intervertebral spacer. The first lobe is elevated outwardly relative to the perimeter wall at the first bone-facing side. The intervertebral spacer includes a solid body and a porous body integrally formed together as a single part, wherein the solid body includes a first solid portion of the first lobe and the porous body includes a first porous portion of the first lobe. The first porous portion of the first lobe is elevated outwardly relative to the first solid portion of the first lobe and the perimeter wall at the first bone-facing side. The system of claim 10, wherein the bone anchor hole is surrounded by a wall that extends the full length of the bone anchor hole between the perimeter wall and the first lobe. The intervertebral spacer includes a solid body and a porous body integrally formed together as a single part, wherein the solid body includes the wall that surrounds the bone anchor hole. The system includes: a locking mechanism; wherein the bone anchor includes a head, wherein the head includes a notch; wherein when the bone anchor is received in the bone anchor hole, the notch engages the locking mechanism to prevent the bone anchor from backing out of the bone anchor hole.

In yet another aspect of the technology an intervertebral implant system includes: an intervertebral spacer including a solid body, a leading side, an opposite trailing side, a first bone-facing side, an opposite second bone-facing side, a right side, and an opposite left side, wherein the solid body includes a perimeter wall, a first lobe, and a bone anchor hole; wherein the perimeter wall extends around the leading, trailing, right, and left sides between the first and second bone-facing sides, wherein the first lobe extends from the perimeter wall across a portion of the first bone-facing side to terminate in a central region of the first bone-facing side, wherein the bone anchor hole extends obliquely through the perimeter wall and the first lobe so that the first lobe surrounds the bone anchor hole; and a bone anchor configured to be received in the bone anchor hole so that a portion of the bone anchor protrudes outwardly from the first bone-facing side.

Embodiments of this aspect of the technology may include one or more of the following attributes. The intervertebral spacer includes a porous body integrally formed together with the solid body as a single part, wherein the perimeter wall surrounds the porous body and abuts a perimeter portion of the porous body. The porous body supports at least a portion of the perimeter wall during fabrication of the intervertebral spacer. The first lobe is elevated outwardly relative to the perimeter wall at the first bone-facing side. The intervertebral spacer includes a porous body integrally formed together with the solid body as a single part, wherein the solid body includes a first solid portion of the first lobe and the porous body includes a first porous portion of the first lobe. The first porous portion of the first lobe is elevated outwardly relative to the first solid portion of the first lobe and the perimeter wall at the first bone-facing side. The bone anchor includes a helically fluted shank having a length, wherein the helical flute has a pitch that is substantially equal to the length. The shank includes at least two helical flutes, each having a land and a neck located interior to the land, wherein the neck is narrower than the land. The system includes: a locking mechanism; wherein the bone anchor includes a head, wherein the head includes a notch; wherein when the bone anchor is received in the bone anchor hole, the notch engages the locking mechanism to prevent the bone anchor from backing out of the bone anchor hole.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 10 is a top view of the solid body of FIG. 8. The bottom view is a mirror image of FIG. 10;

FIG. 11 is a cross-sectional view of the solid body of FIG. 8 taken along section line 11-11 of FIG. 12;

FIG. 12 is a front view of the solid body of FIG. 8;

FIG. 13 is a right view of the solid body of FIG. 8. The left view is a mirror image of FIG. 13;

FIG. 14 is a back view of the solid body of FIG. 8;

FIG. 15 is a cross-sectional view of the solid body of FIG. 8 taken along section line 15-15 of FIG. 12;

FIG. 43 is a top view of the porous body of FIG. 41. The bottom view is a mirror image of FIG. 43;

FIG. 44 is a cross-sectional view of the porous body of FIG. 41 taken along section line 44-44 of FIG. 45;

FIG. 45 is a front view of the porous body of FIG. 41;

FIG. 46 is a right view of the porous body of FIG. 41. The left view is a mirror image of FIG. 46;

FIG. 47 is a back view of the porous body of FIG. 41;

FIG. 48 is a cross-sectional view of the porous body of FIG. 41 taken along section line 48-48 of FIG. 45;

FIG. 49 is a front view of a bone anchor of the intervertebral spacer of FIG. 26;

FIG. 50 is a cross-sectional view of the bone anchor of FIG. 49 taken along section line 50-50 of FIG. 49;

FIG. 51 is an oblique view of the bone anchor of FIG. 49;

FIG. 55A is a top view of another porous body of an intervertebral spacer; and FIG. 55B is an enlarged detail view of a portion of the porous body of FIG. 55A;

FIG. 56A is a front view of the porous body of FIG. 55A; and FIG. 56B is an enlarged detail view of a portion of the porous body of FIG. 56A; and FIG. 57A is a right view of the porous body of FIG. 55A; and FIG. 57B is an enlarged detail view of a portion of the porous body of FIG. 57A.

DETAILED DESCRIPTION

Figure 1:
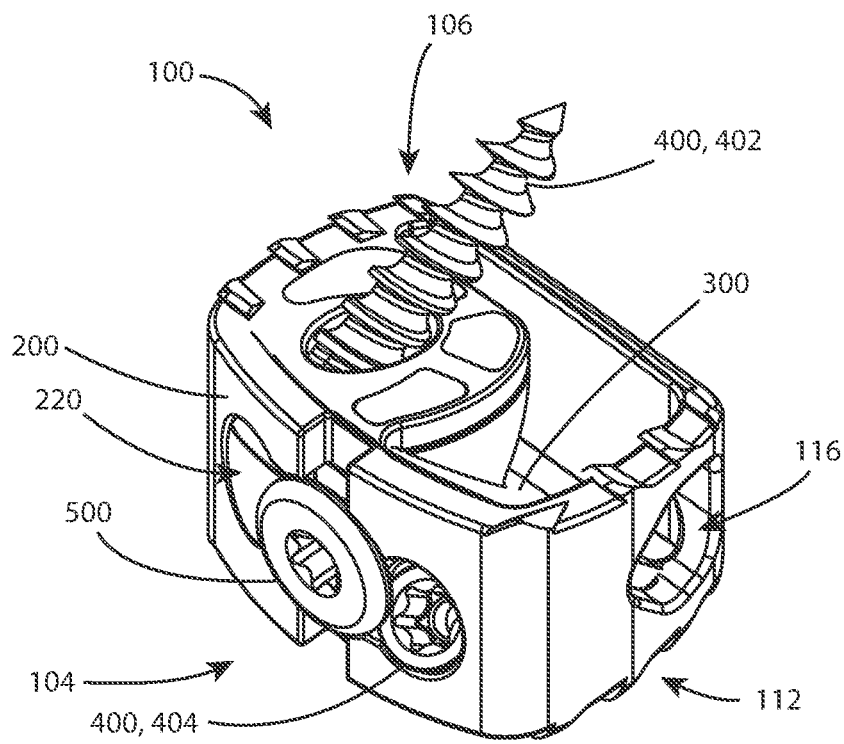
FIG. 1 is an oblique view of an intervertebral spacer implant system with a solid body, a porous body, bone screws, and a locking screw.
Figure 2:
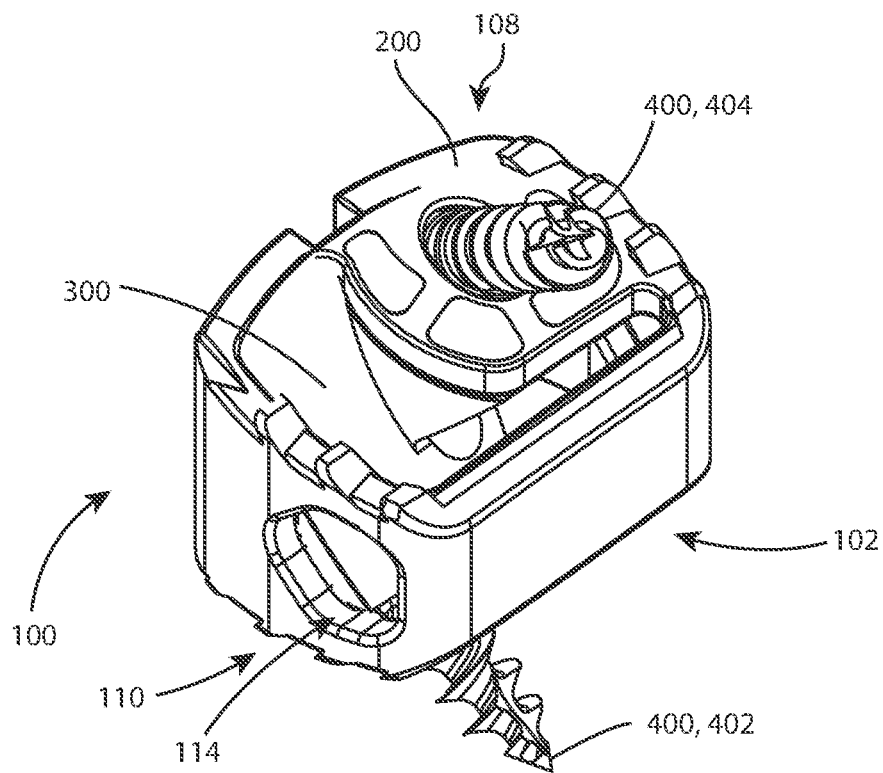
FIG. 2 is another oblique view of the intervertebral spacer of FIG. 1 from a different direction.
Figure 3:
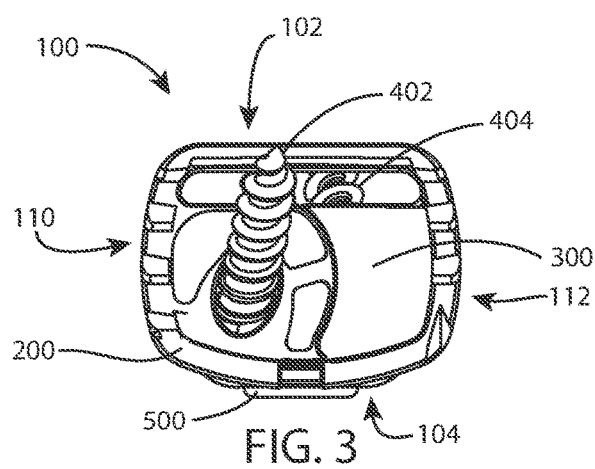
FIG. 3 is a top view of the intervertebral spacer of FIG. 1. The bottom view is a mirror image of FIG. 3.
Figure 4:
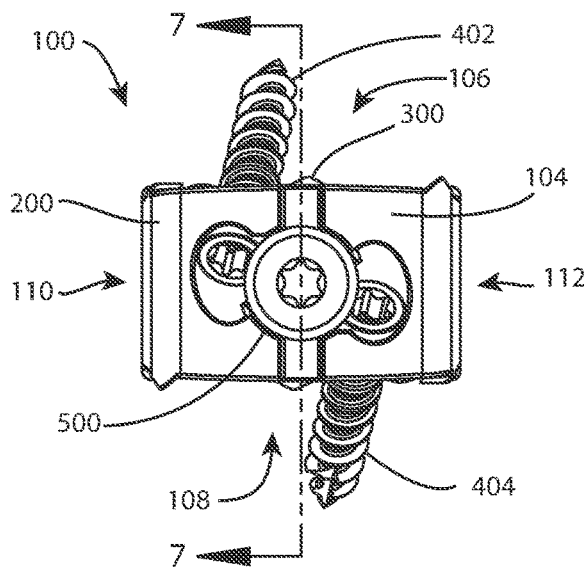
FIG. 4 is a front view of the intervertebral spacer of FIG. 1.
Figure 5:
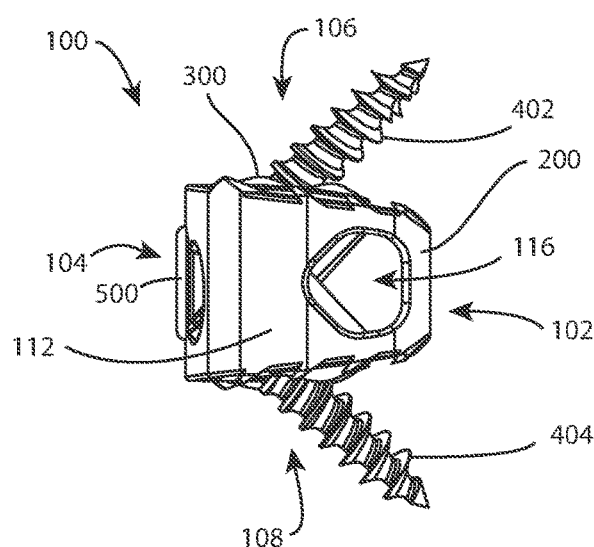
FIG. 5 is a right view of the intervertebral spacer of FIG. 1. The left view is a mirror image of FIG. 5.
Figure 6:
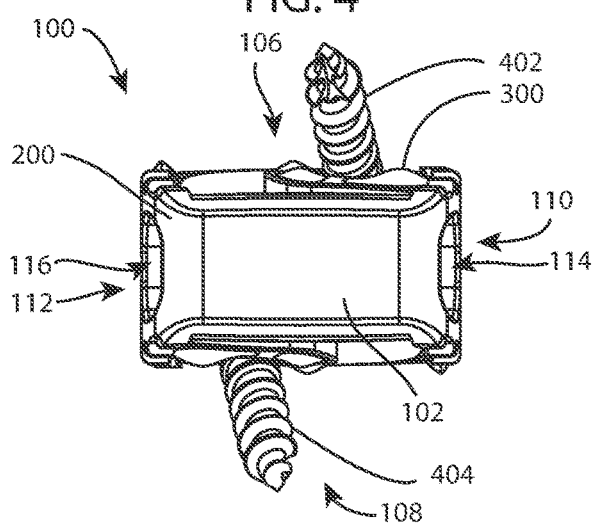
FIG. 6 is a back view of the intervertebral spacer of FIG. 1.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

In this specification, standard spine anatomical and directional terms are employed with their ordinary and customary meanings.

In this specification, "substantially" means within ±10%.

Referring to FIGS. 1-7, an intervertebral spacer implant system 100 may include a solid body 200, a porous body 300, a bone anchor such as a bone screw 400, and/or a locking mechanism such as a locking screw 500. Preferably, the solid body 200 and the porous body 300 may be integrally formed together as a single part, such as by an additive manufacturing process. For the purposes of description, however, the solid body 200 and the porous body 300 will be described and shown as if they are separate parts. The example shows a superior bone screw 402 and an inferior bone screw 404. The bone screws may be replaced by other types of bone anchors. The system 100 has a leading side 102 and a trailing side 104. In this embodiment, the leading side 102 may be a posterior side and the trailing side 104 may be an anterior side so that the system 100 is adapted for an anterior approach to the spine. The system 100 includes a first side 106 that may be considered the top or superior aspect of the system 100 and a second side 108 that may be considered the bottom or inferior aspect of the system 100; however, the top and bottom may also be interchangeable. The first and second sides 106, 108 may be referred to as bone-facing sides of the system 100. The system 100 has a right side 110 and a left side 112; however, the left and right sides may also be interchangeable. There may be an aperture 114 in the right side 110 and an aperture 116 in the left side 112 that may also be interchangeable.

FIGS. 3-7 show the placement and proximity of the components of the system 100; the solid body 200, the porous body 300, the superior bone screw 402, the inferior bone screw 404, and the locking screw 500 that fixes the bone screws 402, 404 in position relative to the solid body 200 and the porous body after screw insertion.

Referring to FIGS. 8-15, the solid body 200 has a leading side 201 and a trailing side 202. In this embodiment, the leading side 201 may be a posterior side and the trailing side 202 may be an anterior side. The solid body 200 has a first side 203 that may be considered the top or superior aspect of the solid body 200 and a second side 204 that may be considered the bottom or inferior aspect of the solid body 200; however, the top and bottom may also be interchangeable. The second side 204 may be identical to the first side 203 as shown, or a mirror image. The solid body 200 has a right side 206 and a left side 208; however, the left and right sides may also be interchangeable. The left side 208 may be a mirror image of the right side 206 as shown. A perimeter wall 207 may extend around the solid body 200 between the first and second sides 203, 204, and may include the leading side 201, the trailing side 202, the right side 206, and the left side 208. There may be an aperture 226 in the right side 206 and an aperture 228 in the left side 208 that may also be interchangeable. The left aperture 228 may be a mirror image of the right aperture 226 as shown.

Figure 8:
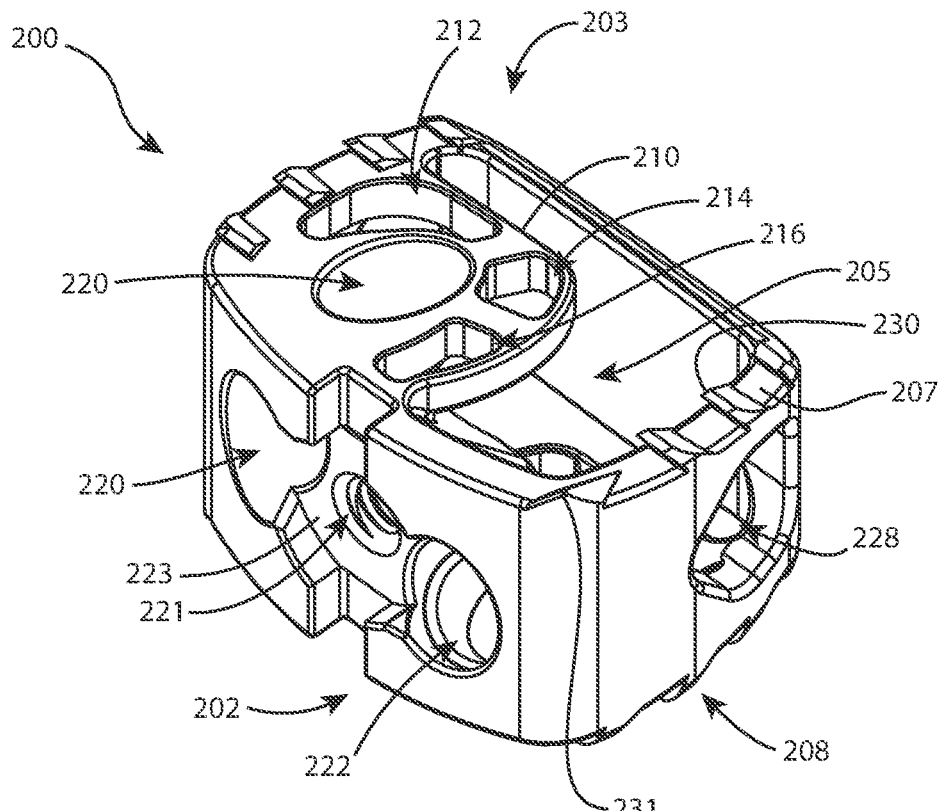
FIG. 8 is an oblique view of a solid body of the intervertebral spacer of FIG. 1.

FIG. 8 is an oblique view showing the trailing side 202, the first side 203, and the left side 208 of the solid body 200. The first side 203 has a perimeter that may have one or more projections 230, such as teeth, serrations, denticles, spikes, prongs, etc. along the left and right portions of the first side 203. The projections 230 extend outwardly from the first side 203 and may be inclined toward the trailing side 202 (FIG. 13). One or more taller projections 231 may also be present on the first side 203. A single projection 231 is shown at the left trailing corner of the first side 203, having a triangular profile (FIG. 12). The first side 203 also includes an asymmetrical overhang or lobe 210 that may also be referred to as a platform, collar, flange, washer, etc. This lobe 210 is adjacent to the trailing side 202 and also adjacent to the right side 206. In other words, the lobe 210 extends from the right trailing portion of the first side 203 toward a central region of the first side 203. The lobe 210 overhangs a central cavity 205 within the solid body 200. The lobe 210 may be cantilevered over the central cavity 205. The lobe 210 provides support around the right bore 220 that receives the superior bone screw 402, and acts as a washer for the bone screw 402, providing increased surface area for vertebral bone contact. Referring to FIGS. 13 and 15, the lobe 210 may protrude outwardly beyond the height of the perimeter wall 207 so that the lobe is elevated above the nominal height of the perimeter wall to make firm contact with the adjacent vertebral endplate. More than one lobe 210 may be present on the first side 203. The superior lobe 210 is shown with three apertures: a right aperture 212 that may be triangular in shape, a middle aperture 214 that may be trapezoidal in shape, and a left aperture 216 that may be rectangular in shape. Any number of apertures may be included, and the apertures may have any shape. The apertures may accommodate the prominences of the porous body 300, discussed below. FIG. 8 shows a right bore 220 for the superior bone screw 402 that extends into the vertebra above the system 100 and a left bore 222 for the inferior bone screw 404 that extends into the vertebra below the system 100. Referring to FIGS. 10 and 12, the right bore 220 extends through the trailing side 202 and the first side 203 along an oblique trajectory from anterior-inferior-lateral to posterior-superior-medial, and the left bore 222 extends through the trailing side 202 and the second side 204 along another oblique trajectory from anterior-superior-lateral to posterior-inferior-medial. The bores 220, 222 may be partially or entirely surrounded by cylindrical walls that extend along the oblique trajectories between the trailing side 202 and the first side 203 and lobe 210 (for bore 222) or between the trailing side 202 and the second side 204 and lobe 232 (for bore 220). See FIGS. 10 and 12. Advantageously, a full-length, full-diameter cylindrical wall stabilizes the bone screws 402, 404 to minimize or eliminate the screw from wobbling. The bores 220, 222 may include features that interact with the bone screws 402, 404 to provide polyaxial angulation of the screws and/or to lock the screws to the solid body 200 and/or the porous body 300. A centralized bore 221 may extend through the trailing side 202 between the left and right bores 220, 222 along a trailing-leading direction. The centralized bore 221 may be internally threaded. A sunken region 223 may surround the centralized bore 221.

Figure 9:
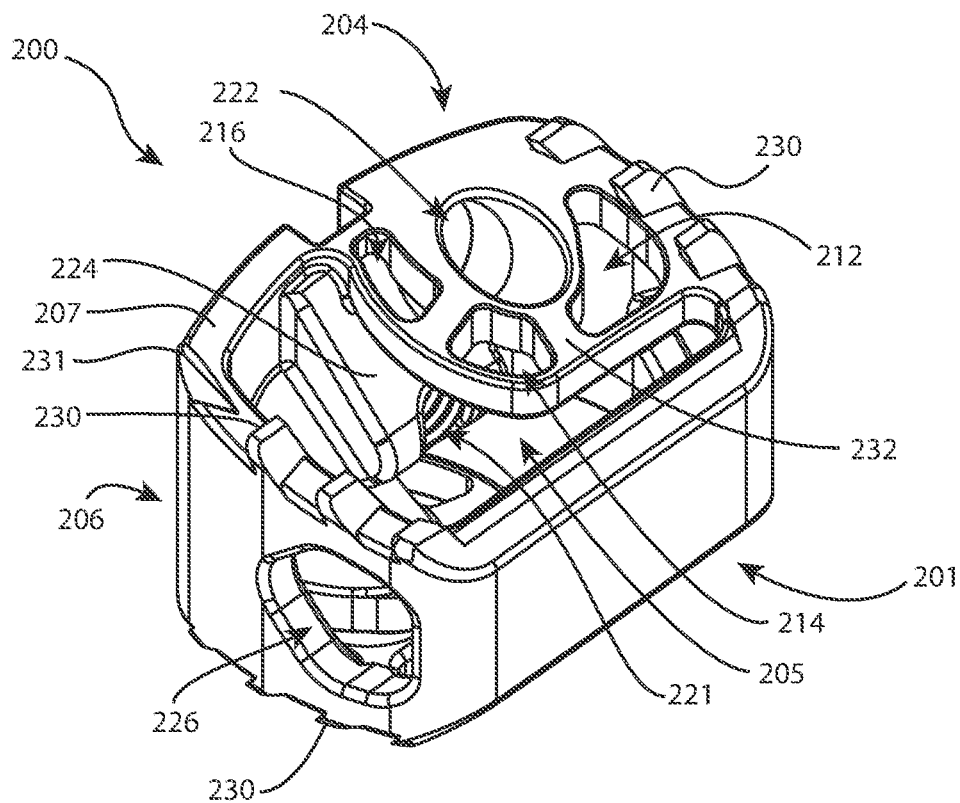
FIG. 9 is another oblique view of the solid body of FIG. 8 from a different direction.

FIG. 9 is another oblique view of the solid body of FIG. 8 showing the leading side 201, the second side 204, and the right side 206. The first side 203 of the solid body 200 (FIG. 8) and the second side 204 of the solid body 200 (FIG. 9) may be identical, interchangeable, or mirror images of each other. An inferior lobe 232 is shown on the second side 204 extending from the left trailing portion of the second side toward a central region of the second side 204. The inferior lobe 232 may be identical to the superior lobe 210, interchangeable, or mirror images. This view shows a supporting structure 224 around the centralized bore 221 that receives the locking screw 500. The supporting structure 224 projects from the trailing side 202 into the central cavity 205 along the trailing-leading direction, and may taper down in height along the trailing-leading direction.

FIGS. 10-15 show the placement of the features of the solid body 200 in relation to the leading side 201 and the trailing side 202; the location of the projections 230, 231 on the perimeters of the first and second sides 203, 204, the superior lobe 210, the inferior lobe 232, the lobal apertures 212, 214, 216, the right bore 220, the left bore 222, and the centralized bore 221. FIG. 15 is a cross-sectional view along section line 15-15 of FIG. 12, showing the depth of the centralized bore 221 that accepts the locking screw 500 and the surrounding supporting structure 224.

Referring to FIGS. 16-23, the porous body 300 has a leading side 301 and a trailing side 302. In this embodiment, the leading side 301 may be a posterior side and the trailing side 302 may be an anterior side. The porous body 300 has a first side 303 that may be considered the top or superior aspect of the porous body 300 and a second side 304 that may be considered the bottom or inferior aspect of the porous body 300; however, the top and bottom may also be interchangeable. The second side 304 may be identical to the first side 303, or a mirror image. The porous body 300 has a right side 306 and a left side 308; however, the left and right sides may also be interchangeable. The left side 308 may be a mirror image of the right side 306 as shown.

Figure 16:
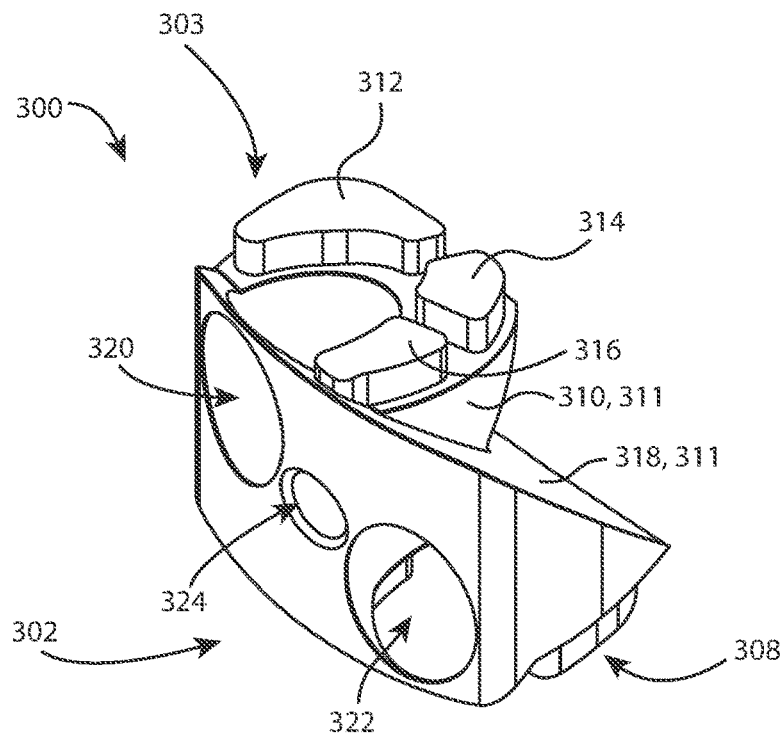
FIG. 16 is an oblique view of a porous body of the intervertebral spacer of FIG. 1.

FIG. 16 is an oblique view of the porous body 300 showing the trailing side 302, the first side 303, and the left side 308. The trailing side 302 includes a right bore 320 that surrounds the right bore 220 of the solid body 200, and a left bore 322 that surrounds the left bore 222 of the solid body 200. The trailing side 302 also includes a centralized bore 324 that surrounds the centralized bore 221 of the solid body 200. The centralized bore 324 may be sized and shaped to receive the supporting structure 224 of the solid body. Alternatively, at least for embodiments that are fabricated by additive manufacturing operations, the bore 324 may have an inside diameter that is larger than the major diameter of the internal threads of the bore 221, as shown. The first side 303 of the porous body 300 features a superior porous structure 310 with three raised prominences of porous material: a superior right prominence 312 which may be triangular in shape, a superior middle prominence 314 which may be trapezoidal in shape, and a superior left prominence 316 which may be rectangular in shape. Any number of prominences may be included, and the prominences may have any shape. Preferably, the number and shape of the prominences corresponds to the number and shape of the lobal apertures of the solid body 200. Referring to FIGS. 20-23, each prominence may include a domed or bulging superior surface to enhance contact with the adjacent vertebral endplate. The superior porous structure 310 may include a pedestal 311 that extends internally from the first side 303. The pedestal may taper toward the trailing side 302 as it extends. The first side 303 of the porous body 300 and the second side 304 of the porous body 300 are interchangeable.

Figure 17:
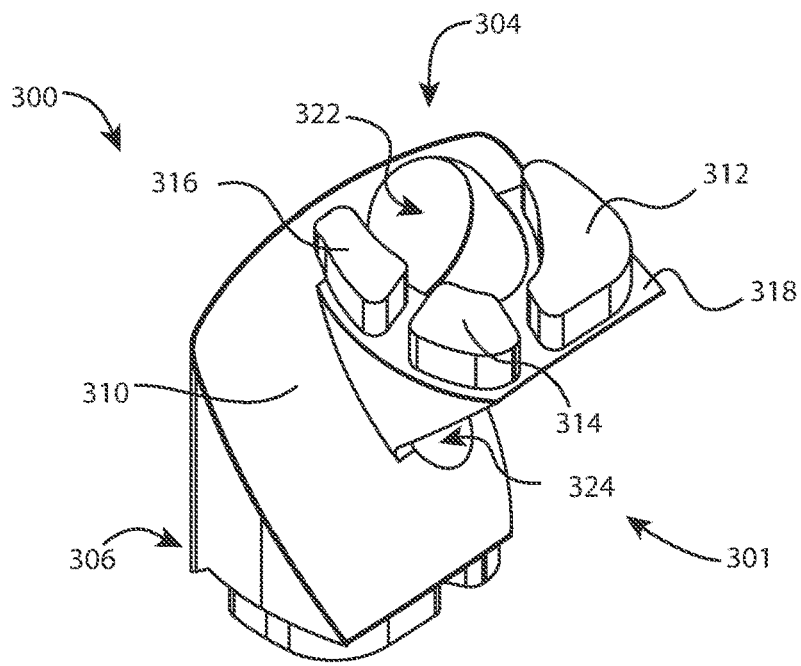
FIG. 17 is another oblique view of the porous body of FIG. 16 from a different direction.
Figure 18:
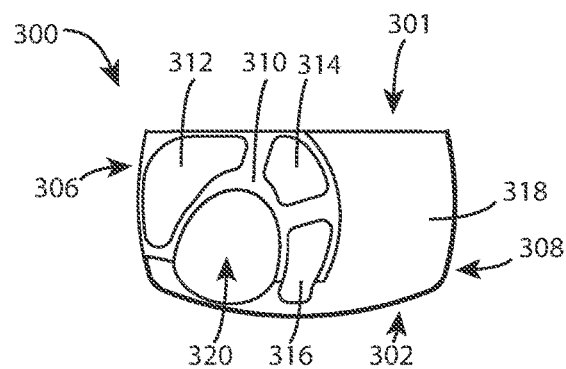
FIG. 18 is a top view of the porous body of FIG. 16. The bottom view is a mirror image of FIG. 18.
Figure 19:
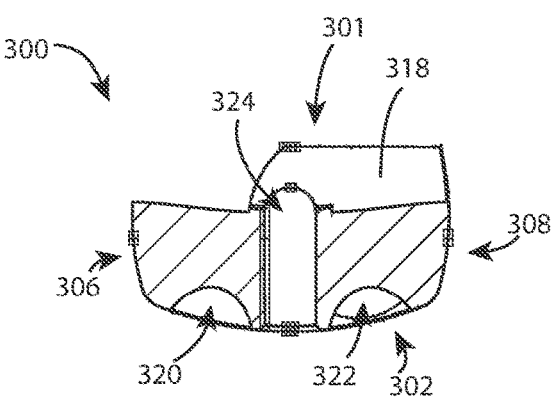
FIG. 19 is a cross-sectional view of the porous body of FIG. 16 taken along section line 19-19 of FIG. 20.
Figure 20:
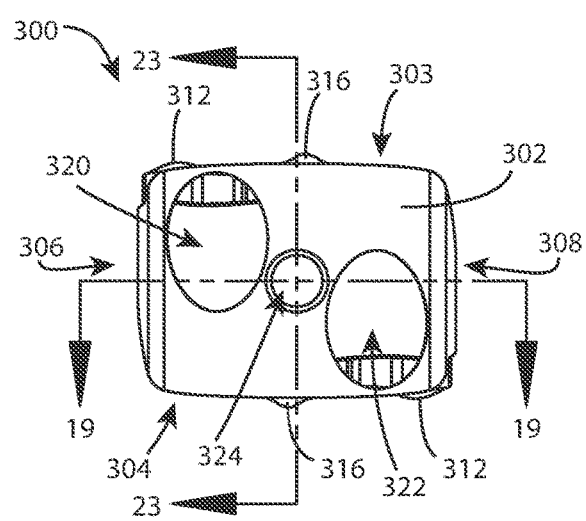
FIG. 20 is a front view of the porous body of FIG. 16.

FIG. 17 is another oblique view of the porous body of FIG. 16 showing the leading side 301, the second side 304, and the right side 306. The porous body 300 includes an inferior porous structure 318 which may be identical to the superior porous structure 310 as shown, interchangeable, or mirror images. The first side 303 of the porous body 300 is a mirror image of the second side 304 of the porous body 304 and may be interchangeable.

Figure 21:
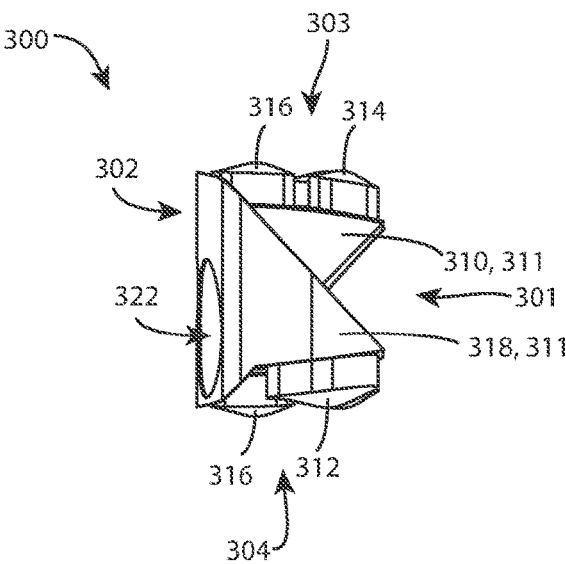
FIG. 21 is a right view of the porous body of FIG. 16. The left view is a mirror image of FIG. 21.
Figure 22:
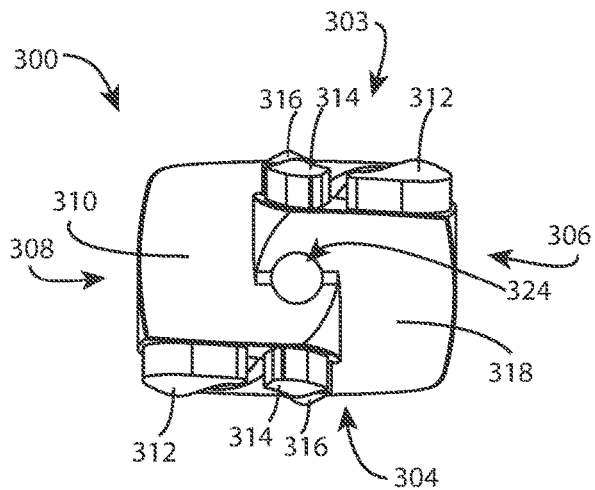
FIG. 22 is a back view of the porous body of FIG. 16.
Figure 23:
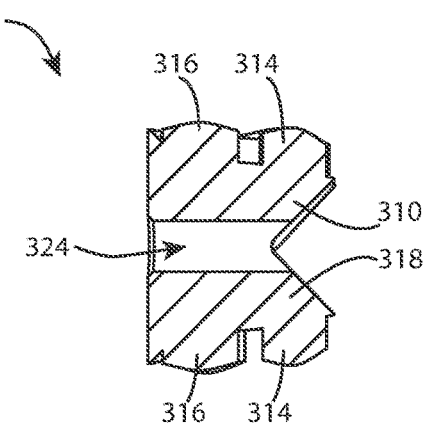
FIG. 23 is a cross-sectional view of the porous body of FIG. 16 taken along section line 23-23 of FIG. 20.

FIGS. 18-23 show the structure of the porous body 300 indicating the placement of the superior porous structure 310 and the inferior porous structure 318. The second side 304 is the mirror image of the first side 303. FIG. 21 depicts the mounding on top of the superior and inferior prominences 312, 314, 316. The porous prominences on both the first side 303 and the second side 304 are seated within the lobal apertures of the solid body 200 in such a way that the mounds on top of the prominences may extend above, or outward from, the surfaces of the lobes of the solid body 200. This extension allows the vertebral bone to contact the porous body first under compression to promote bone growth into the porous material. FIG. 23 is a cross-sectional view of FIG. 20 along section line 23-23 that shows the centralized bore 324.

Figure 24:
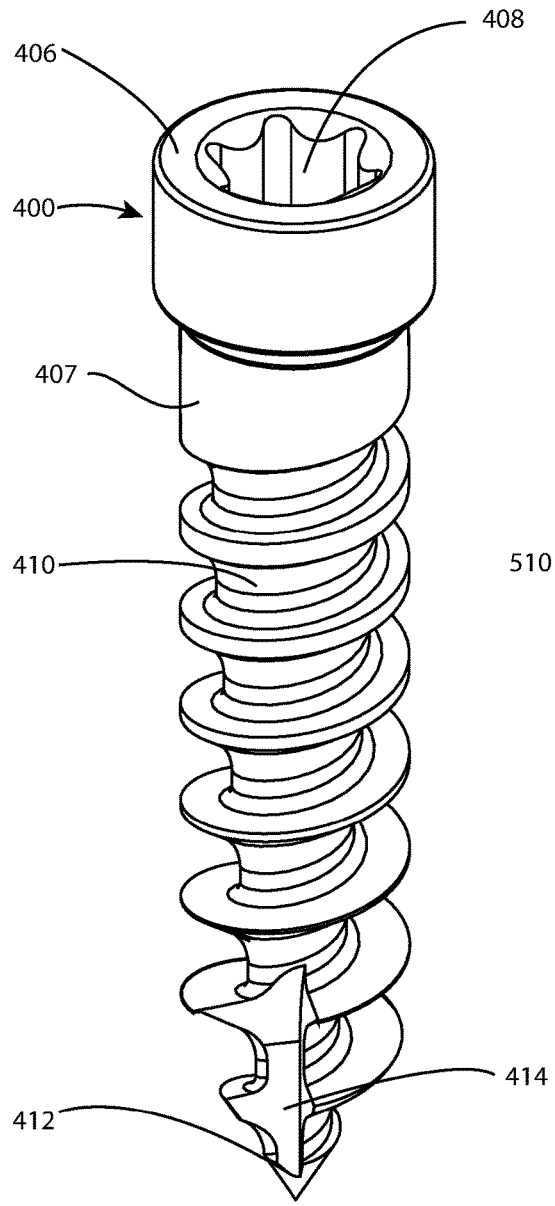
FIG. 24 is an oblique view of a bone screw of the intervertebral spacer of FIG. 1.

Referring to FIG. 24, a bone screw 400 has a head 406 that contains a drive feature 408 to receive torque from a screw driver (not shown). Below the head 406 is a smooth shank 407 or shaft. Below the smooth shank is a threaded shank 410 or shaft that may have a tapered end 412 and may have a self-tapping feature 414 that allows the screw 400 to be driven into the vertebral bone without pre-drilling. The inferior bone screw 404 may be identical to the superior bone screw 402.

Figure 7:
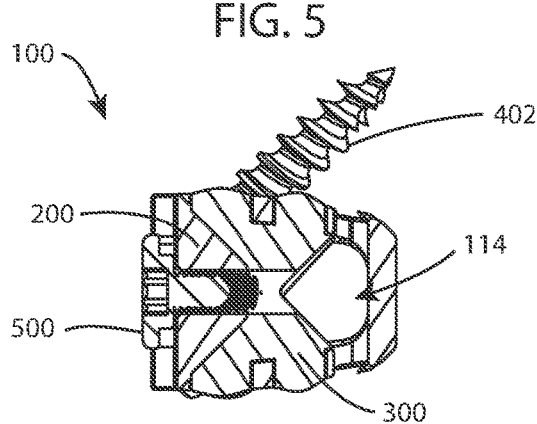
FIG. 7 is a cross-sectional view of the intervertebral spacer of FIG. 1 taken along section line 7-7 of FIG. 4.
Figure 25:
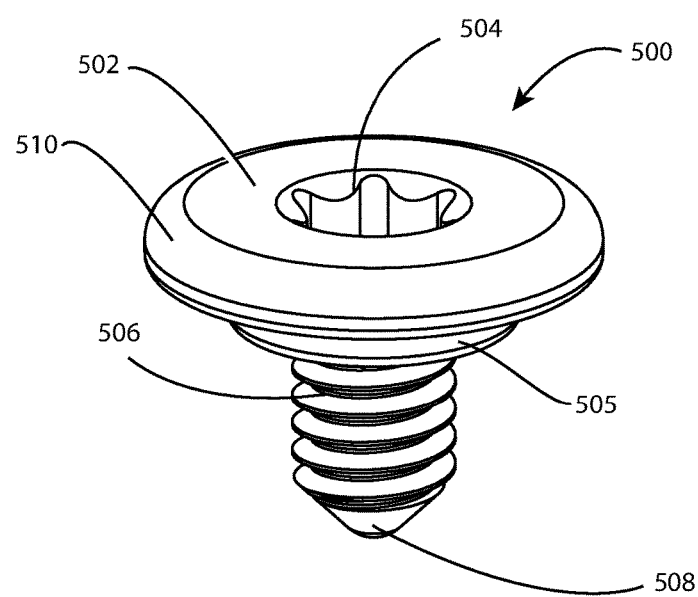
FIG. 25 is an oblique view of a locking screw of the intervertebral spacer of FIG. 1.
Figure 26:
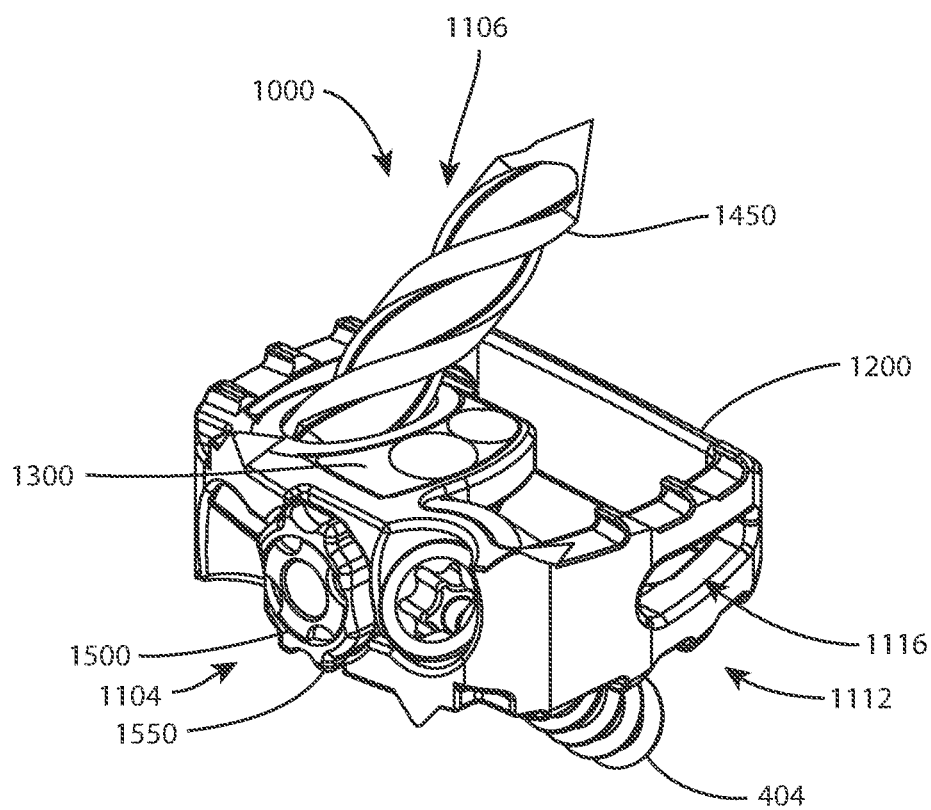
FIG. 26 is an oblique view of another intervertebral spacer implant system with a solid body, a porous body, bone anchors, and a fastener locking mechanism.
Figure 27:
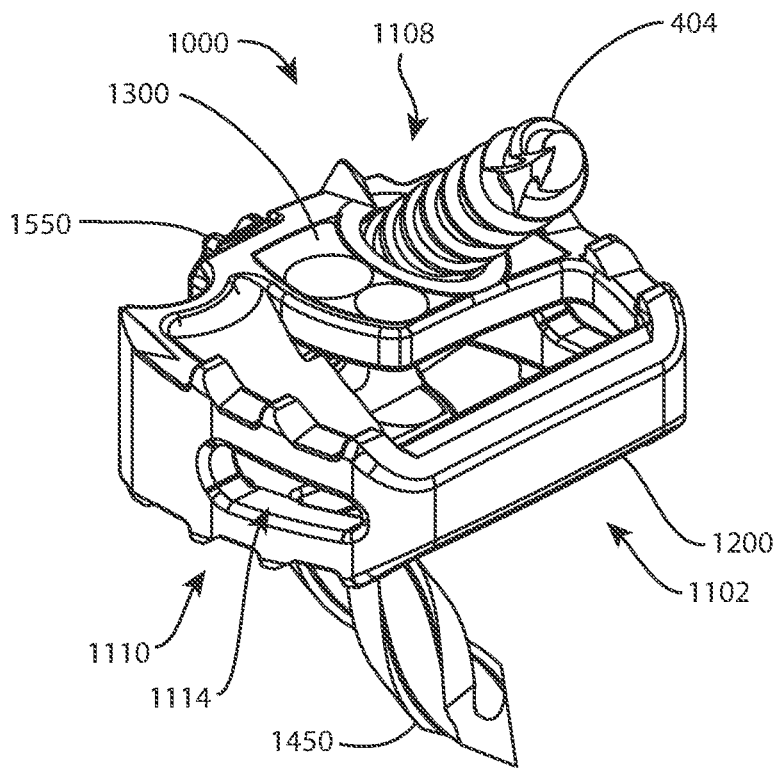
FIG. 27 another oblique view of the intervertebral spacer of FIG. 26 from a different direction.
Figure 28:
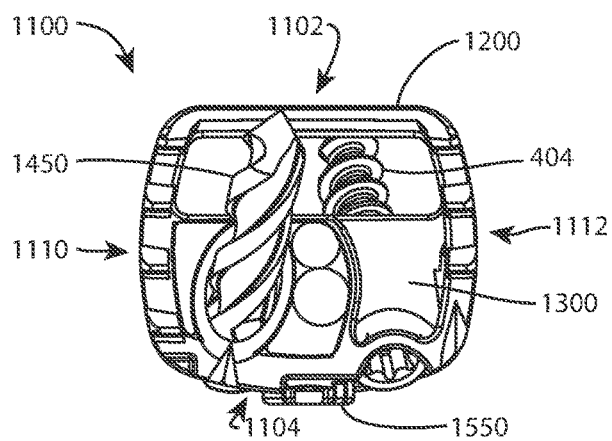
FIG. 28 is a top view of the intervertebral spacer of FIG. 26. The bottom view is a mirror image of FIG. 28.
Figure 29:
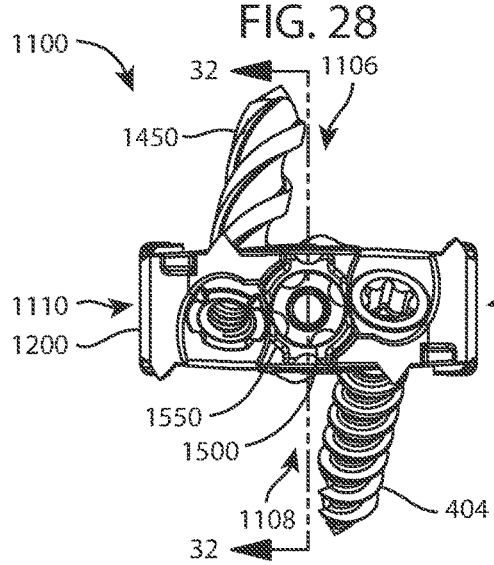
FIG. 29 is a front view of the intervertebral spacer of FIG. 26.
Figure 30:
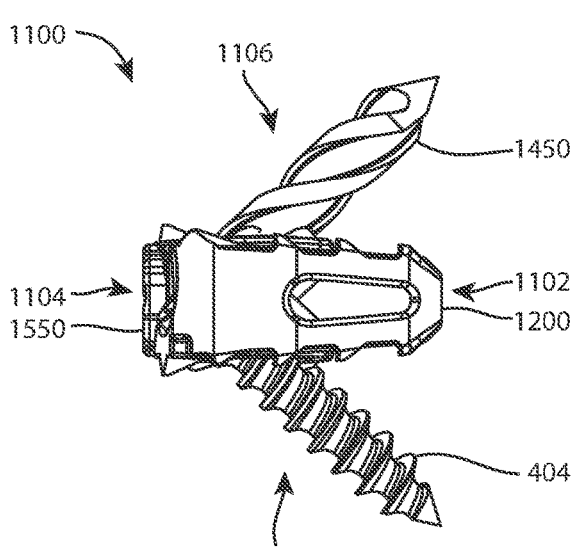
FIG. 30 is a right view of the intervertebral spacer of FIG. 26. The left view is a mirror image of FIG. 30.
Figure 31:
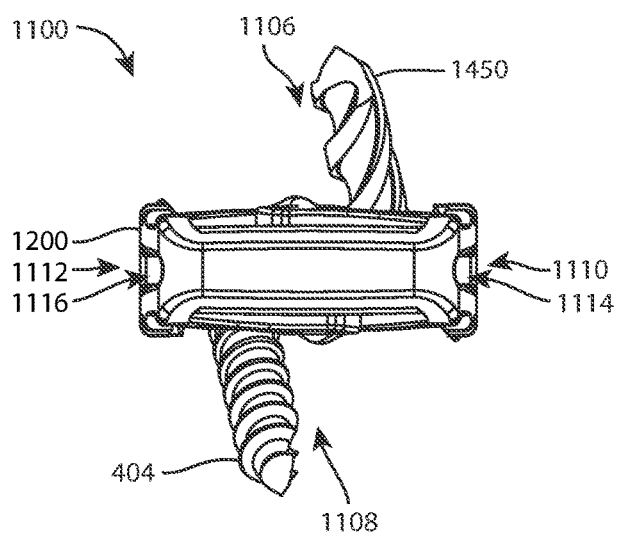
FIG. 31 is a back view of the intervertebral spacer of FIG. 26.

Referring to FIGS. 7 and 25, the locking screw 500 has a head 502 that contains a drive feature 504 to receive torque from a screw driver (not shown). Below the head 502 is a smooth shank 505 or shaft. Below the smooth shank is a threaded shank 506 or shaft that may have a tapered end 508. The head 502 of the locking screw 500 has a rounded or tapered edge 510 to reduce contact with or injury to vertebral or neurovascular structures.

The solid body 200 and the porous body 300 may be fabricated together at the same time via additive manufacturing technology. Thus, the disclosed solid body 200 and porous body 300 may be superimposed or "occupy the same space." The solid body 200 may be fully dense or non-porous, or it may be distinctly more dense or less porous than the porous body 300. The solid body 200 may be 80% to 100% dense. The porous body 300 may be 80%±10% dense or 80%±5% dense. The porous body 300 may have one or more pore sizes and/or shapes which are favorable for bone ongrowth/ingrowth. The porous body 300 may have a consistent porous structure throughout, or there may be one or more gradients or abrupt changes in porous structure. The porous body 300 may provide sufficient internal support structure to the solid body lobes so that no additional temporary support structure is required to ensure that the solid body builds according to specifications. Preferably, the taper angles of the pedestals 311 of the porous body 300 may be selected to be compatible with the taper angles that a given additive manufacturing system will build without additional temporary support structure and with satisfactory finished product. Preferably, the taper angles of the pedestals 311 of the porous body 300 may be 45° or less. In one example, the solid body 200 and the porous body 300 may be fabricated together by additive manufacturing with the solid and porous bodies 200, 300 superimposed and oriented so that the leading side 201 is the base on which the bodies are built or printed, in other words, the first layer of the build, and the trailing side 202 includes the last layer of the build. In another example, the trailing side 202 includes the first layer of the build and the leading side 201 includes the last layer of the build.

The centralized bore 324 of the porous body surrounds the centralized bore 221 of the solid body, and may optionally receive the supporting structure 224. The right bore 320 surrounds the right bore 220. The left bore 322 surrounds the left bore 222. The superior porous structure 310 supports the superior lobe 210. The inferior porous structure 318 supports the inferior lobe 232. The porous prominences 312, 314, 316 may extend outwardly through the apertures 212, 214, 216, respectively, as shown. Alternatively, the solid structure of the lobes 210, 232 may extend outwardly past the porous structures 310, 318 and corresponding prominences 312, 314, 316. The porous body 300 may fill only a portion of the central cavity 205 of the solid body, so that a portion of the cavity 205 remains empty to receive bone graft or other therapeutic agents. Preferably, the empty portion of the cavity 205 extends through the interconnected solid and porous bodies 200, 300 along a superior-inferior direction. The porous body 300, or at least the superior and inferior porous structures 310, 318, may be flexible enough to permit the lobes 210, 232 to flex inwardly toward a central transverse plane of the implant under compressive loads applied by adjacent superior and inferior vertebrae. The central transverse plane of the implant is represented by section line 11-11 of FIG. 12 and section line 19-19 of FIG. 20. The central sagittal plane of the implant is represented by section lines 7-7 of FIG. 4, 15-15 of FIG. 12, and 23-23 of FIG. 20.

A method of implanting the intervertebral spacer may include some or all of the following steps in any order: creating a surgical access to an operative site, removing a disc from between adjacent superior and inferior vertebrae, inserting the solid/porous spacer along a trailing-leading direction into the prepared disc space, optionally drilling for the bone screw(s), inserting the bone screws through the bores 220, 222 and into the vertebral bodies, and after the bone screws are fully inserted, inserting the locking screw into the bore 221 along the trailing-leading direction, and closing the surgical access.

Referring to FIGS. 26-32, an intervertebral spacer implant system 1100 may include a solid body 1200, a porous body 1300, a bone anchor such as the bone screw 404 or a helical blade 1450, and/or a locking mechanism, such as a bushing 1500 and/or a collar 1550. Preferably, the solid body 1200 and the porous body 1300 may be integrally formed together as a single part, such as by an additive manufacturing process. For the purposes of description, however, the solid body 1200 and the porous body 1300 will be described and shown as if they are separate parts. The example shows a superior helical blade 1450 and an inferior bone screw 404. The bone anchors may be interchangeable, or they may be replaced by other types of bone fasteners. The system 1100 has a leading side 1102 and a trailing side 1104. In this embodiment, the leading side 1102 may be a posterior side and the trailing side 1104 may be an anterior side so that the system 1100 is adapted for an anterior approach to the spine. The system 1100 includes a first side 1106 that may be considered the top or superior aspect of the system 1100 and a second side 1108 that may be considered the bottom or inferior aspect of the system 1100; however, the top and bottom may also be interchangeable. The first and second sides 1106, 1108 may be referred to as bone-facing sides of the system 1100. The system 1100 has a right side 1110 and a left side 112; however, the left and right sides may also be interchangeable. There may be an aperture 1114 in the right side 1110 and an aperture 1116 in the left side 1112 that may also be interchangeable.

FIGS. 28-32 show the placement and proximity of the components of the system 1100; the solid body 1200, the porous body 1300, the superior helical blade 1450, the inferior bone screw 404, the bushing 1500, and the collar 1550.

Referring to FIGS. 33-40, the solid body 1200 has a leading side 1202 and a trailing side 1204. In this embodiment, the leading side 1202 may be a posterior side and the trailing side 1204 may be an anterior side. The solid body 1200 has a first side 1206 that may be considered the top or superior aspect of the solid body 1200 and a second side 1208 that may be considered the bottom or inferior aspect of the solid body 1200; however, the top and bottom may also be interchangeable. The second side 1208 may be identical to the first side 1206 as shown, or a mirror image. The solid body 1200 has a right side 1210 and a left side 1212; however, the left and right sides may also be interchangeable. The left side 1212 may be a mirror image of the right side 1210 as shown. A perimeter wall 1218 may extend around the solid body 1200 between the first and second sides 1206, 1208, and may include the leading side 1202, the trailing side 1204, the right side 1210, and the left side 1212. There may be an aperture 1214 in the right side 1210 and an aperture 1216 in the left side 1212 that may also be interchangeable. The left aperture 1216 may be a mirror image of the right aperture 1214 as shown.

Figure 33:
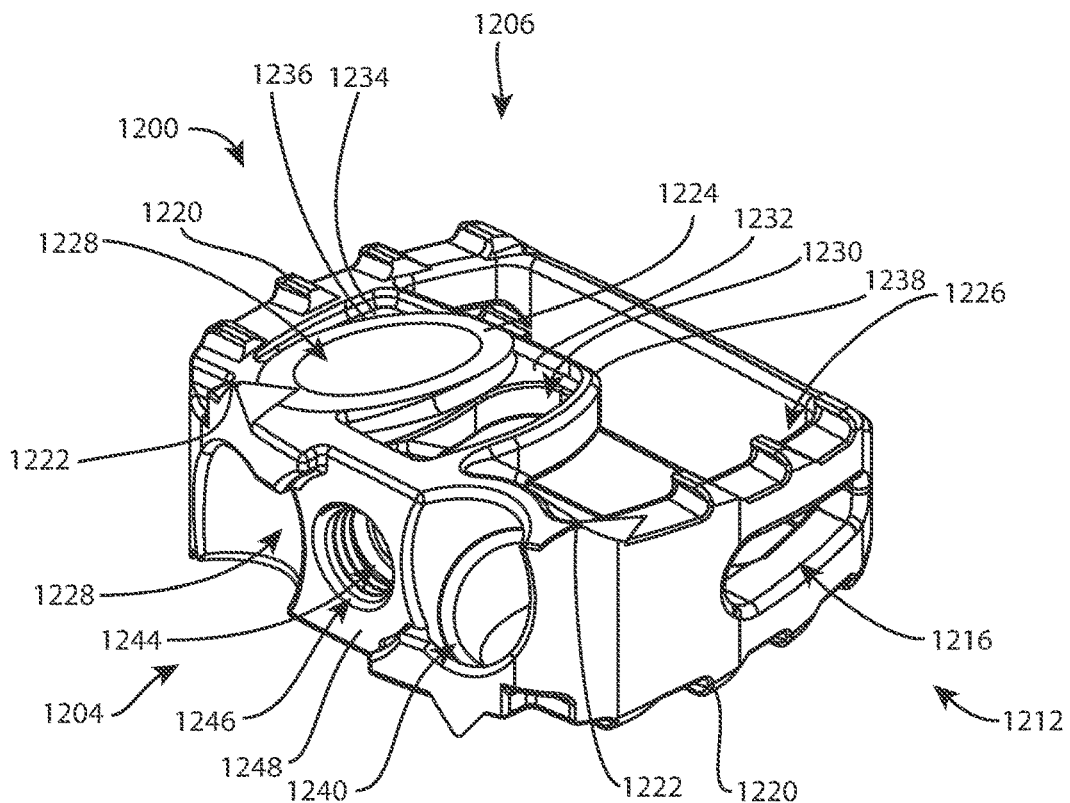
FIG. 33 is an oblique view of a solid body of the intervertebral spacer of FIG. 26.
Figure 35:
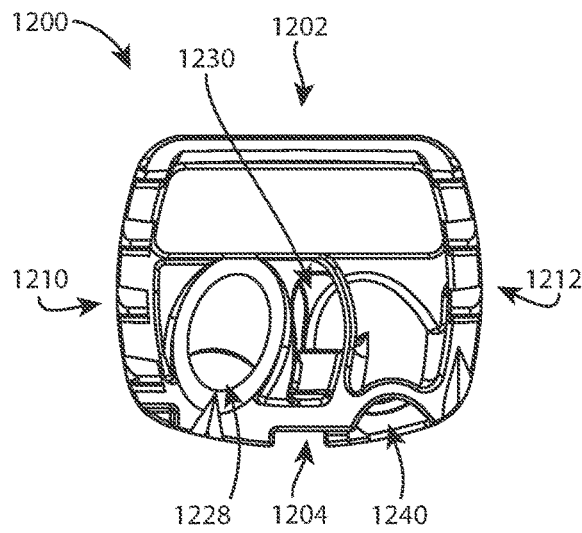
FIG. 35 is a top view of the solid body of FIG. 33. The bottom view is a mirror image of FIG. 35.
Figure 36:
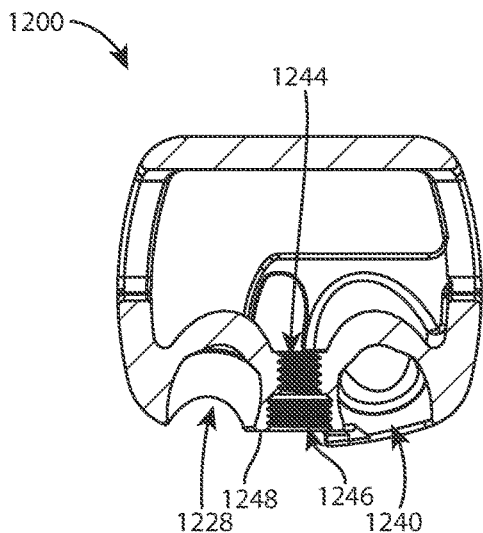
FIG. 36 is a cross-sectional view of the solid body of FIG. 33 taken along section line 36-36 of FIG. 37.
Figure 37:
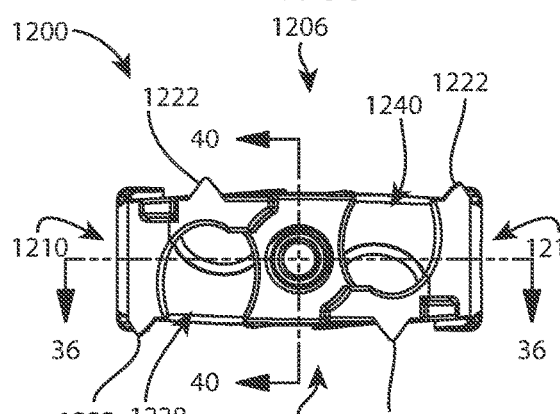
FIG. 37 is a front view of the solid body of FIG. 33.
Figure 38:
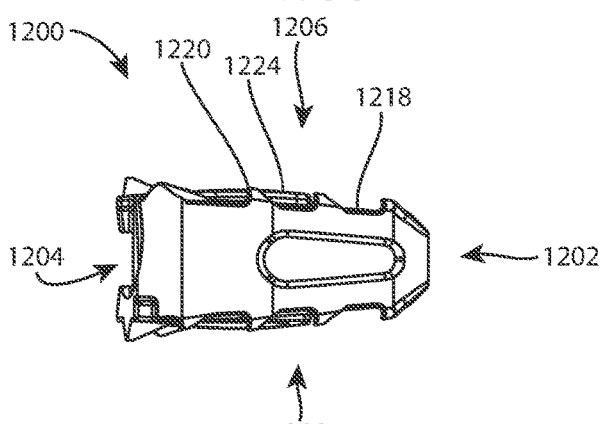
FIG. 38 is a right view of the solid body of FIG. 33. The left view is a mirror image of FIG. 38.
Figure 39:
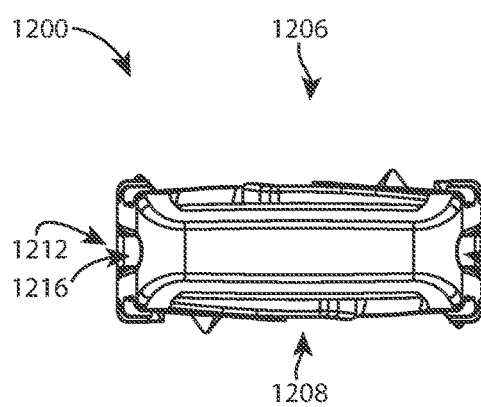
FIG. 39 is a back view of the solid body of FIG. 33.
Figure 40:
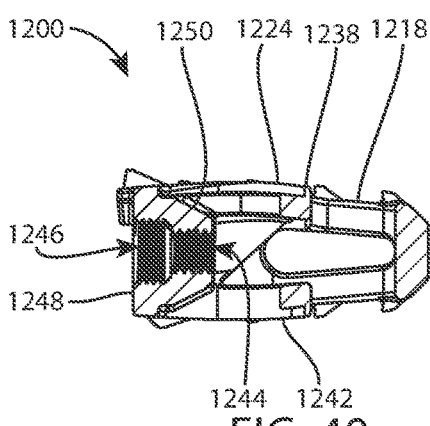
FIG. 40 is a cross-sectional view of the solid body of FIG. 33 taken along section line 40-40 of FIG. 37.

FIG. 33 is an oblique view showing the trailing side 1204, the first side 1206, and the left side 1212 of the solid body 1200. The first side 1206 has a perimeter that may have one or more projections 1220, such as teeth, serrations, denticles, spikes, prongs, etc. along the left and right portions of the first side 1206. The projections 1220 extend outwardly from the first side 1206 and may be inclined toward the trailing side 1204 (FIG. 38). One or more taller projections 1222 may also be present on the first side 1206. Projections 1222 are shown at the trailing edge near the right trailing corner and at the left trailing corner of the first side 1206, having a triangular profile (FIG. 37). The first side 1206 also includes an asymmetrical overhang or lobe 1224 that may also be referred to as a platform, collar, flange, washer, etc. This lobe 1224 is adjacent to the trailing side 1204 and also adjacent to the right side 1210. In other words, the lobe 1224 extends from the right trailing portion of the first side 1206 toward a central region of the first side 1206. The lobe 1224 overhangs a central cavity 1226 within the solid body 1200. The lobe 1224 may be cantilevered over the cavity 1226. The lobe 1224 provides support around the right bore 1228 that receives the superior helical blade 1450, and acts as a washer for the helical blade 1450, providing increased surface area for vertebral bone contact. Referring to FIGS. 38 and 40, the lobe 1224 may protrude outwardly beyond the height of the perimeter wall 1218 so that the lobe is elevated above the nominal height of the perimeter wall to make firm contact with the adjacent vertebral endplate. More than one lobe 1224 may be present on the first side 1206. The superior lobe 1224 is shown with an aperture 1230 that may be rectangular in shape and may be centrally located between the right and left sides 1210, 1212. Any number of apertures may be included, and the apertures may have any shape. The aperture(s) may accommodate the prominences of the porous body 1300, discussed below. The superior lobe 1224 may include one or more sunken regions, such as the sunken region 1232 associated with the aperture 1230 and/or the sunken region 1234 to the right of the right bore 1228. However, a wall 1236 may remain at the full height of the lobe 1224, encircling the right bore 1228; another wall 1238 may remain at the full height of the lobe, extending along the left and leading sides of the lobe. FIG. 33 shows a right bore 1228 for the superior helical blade 1450 that extends into the vertebra above the system 1100 and a left bore 1240 for the inferior bone screw 404 that extends into the vertebra below the system 1100. Referring to FIGS. 35 and 37, the right bore 1228 extends through the trailing side 1204 and the first side 1206 along an oblique trajectory from anterior-inferior-lateral to posterior-superior-medial, and the left bore 1240 extends through the trailing side 1204 and the second side 1208 along another oblique trajectory from anterior-superior-lateral to posterior-inferior-medial. The bores 1228, 1240 may be partially or completely surrounded by cylindrical walls that extend along the oblique trajectories between the trailing side 1204 and the first side 1206 and lobe 1224 (for bore 1240) or between the trailing side 1204 and the second side 1208 and lobe 1242 (for bore 1228). Advantageously, a full-length, full-diameter cylindrical wall stabilizes the bone anchors 1450, 404 to minimize or eliminate the fasteners from wobbling. The bores 1228, 1240 may include features that interact with the bone anchors 1450, 404 to provide polyaxial angulation of the fasteners and/or to lock the fasteners to the solid body 1200 and/or the porous body 1300. A centralized bore 1244 may extend through the trailing side 1204 between the left and right bores 1228, 1240 along a trailing-leading direction. The centralized bore 1244 may be internally threaded. A counterbore 1246 may be associated with the centralized bore 1244; the counterbore 1246 may be internally threaded to receive the bushing 1500. A sunken region 1248 may surround the centralized bore 1244 and/or counterbore 1246.

Figure 34:
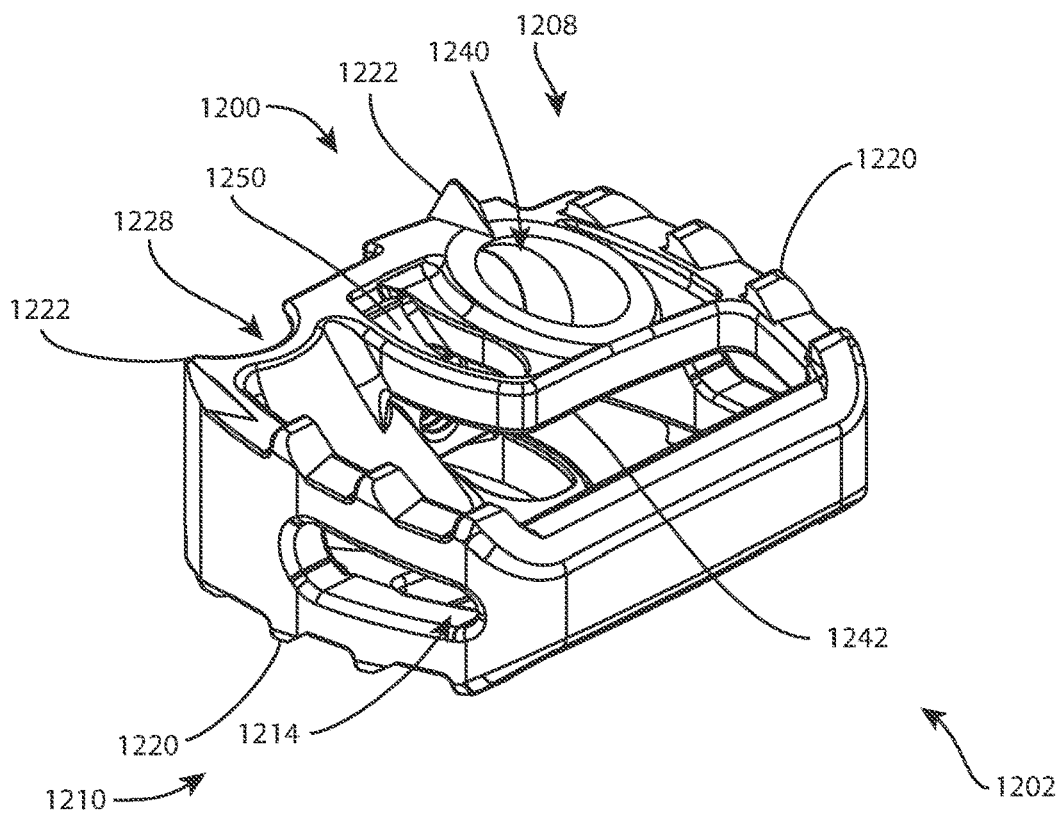
FIG. 34 is another oblique view of the solid body of FIG. 33 from a different direction.

FIG. 34 is another oblique view of the solid body 1200 of FIG. 33 showing the leading side 1202, the second side 1208, and the right side 1210. The first side 1206 of the solid body 1200 (FIG. 33) and the second side 1208 of the solid body 1200 (FIG. 34) may be identical, interchangeable, or mirror images of each other. An inferior lobe 1242 is shown on the second side 1208 extending from the left trailing portion of the second side toward a central region of the second side 1208. The inferior lobe 1242 may be identical to the superior lobe 1224, interchangeable, or mirror images. This view shows a supporting structure 1250 around the centralized bore 1244. The supporting structure 1250 projects from the trailing side 1204 into the central cavity 1226 along the trailing-leading direction, and may taper down in height along the trailing-leading direction.

FIGS. 35-40 show the placement of the features of the solid body 1200 in relation to the leading side 1202 and the trailing side 1204; the location of the projections 1220, 1222 on the perimeters of the first and second sides 1206, 1208, the superior lobe 1224, the inferior lobe 1242, the lobal aperture 1230, the right bore 1228, the left bore 1240, and the centralized bore 1244. FIG. 40 is a cross-sectional view along section line 40-40 of FIG. 37, showing the depth of the centralized bore 1244 and the surrounding supporting structure 1250.

Referring to FIGS. 41-48, the porous body 1300 has a leading side 1302 and a trailing side 1304. In this embodiment, the leading side 1302 may be a posterior side and the trailing side 1304 may be an anterior side. The porous body 1300 has a first side 1306 that may be considered the top or superior aspect of the porous body 1300 and a second side 1308 that may be considered the bottom or inferior aspect of the porous body 1300; however, the top and bottom may also be interchangeable. The second side 1308 may be identical to the first side 1306, or a mirror image. The porous body 1300 has a right side 1310 and a left side 1312; however, the left and right sides may also be interchangeable. The left side 1312 may be a mirror image of the right side 1310 as shown.

Figure 41:
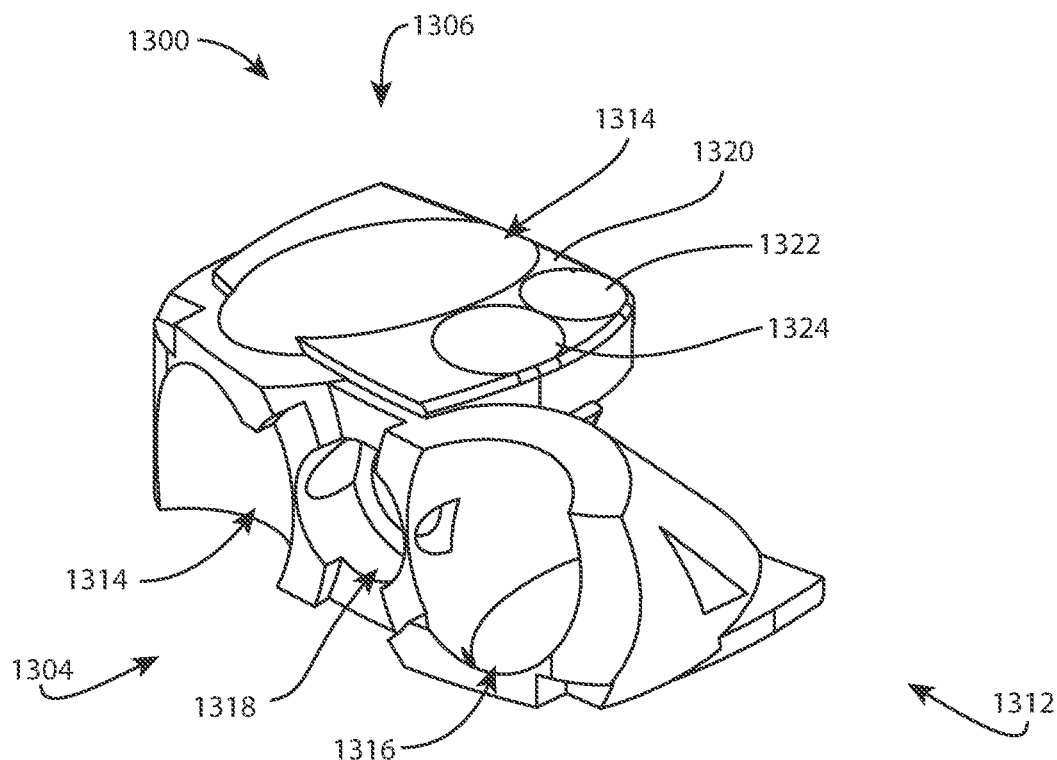
FIG. 41 is an oblique view of a porous body of the intervertebral spacer of FIG. 26.

FIG. 41 is an oblique view of the porous body 1300 showing the trailing side 1304, the first side 1306, and the left side 1312. The trailing side 1304 includes a right bore 1314 that surrounds the right bore 1228 of the solid body 1200, and a left bore 1316 that surrounds the left bore 1240 of the solid body 1200. The trailing side 1304 also includes a centralized bore 1318 that surrounds the centralized bore 1244 of the solid body 1200. The centralized bore 1318 may be sized and shaped to receive the supporting structure 1250 of the solid body. Alternatively, at least for embodiments that are fabricated by additive manufacturing operations, the bore 1318 may have an inside diameter that is larger than the major diameter of the internal threads of the bore 1244 and/or the counterbore 1246. The first side 1306 of the porous body 1300 features a superior porous structure 1320 with one or more raised prominences of porous material: a leading prominence 1322 and a trailing prominence 1324 are shown, both having a round shape and both fitting within the lobal aperture 1230 (see FIG. 26). Any number of prominences may be included, and the prominences may have any shape. Preferably, the number and shape of the prominences may correspond to the number and shape of the lobal aperture(s) of the solid body 1200. Referring to FIGS. 45-48, each prominence may include a domed or bulging superior surface to enhance contact with the adjacent vertebral endplate. The superior porous structure 1320 may include a pedestal 1326 that extends internally from the first side 1306. The pedestal may taper toward the trailing side 1304 as it extends. The pedestal 1326 may form a wall around the right bore 1314. The first side 1306 of the porous body 1300 and the second side 1308 of the porous body 1300 are interchangeable, identical, or mirror images.

Figure 42:
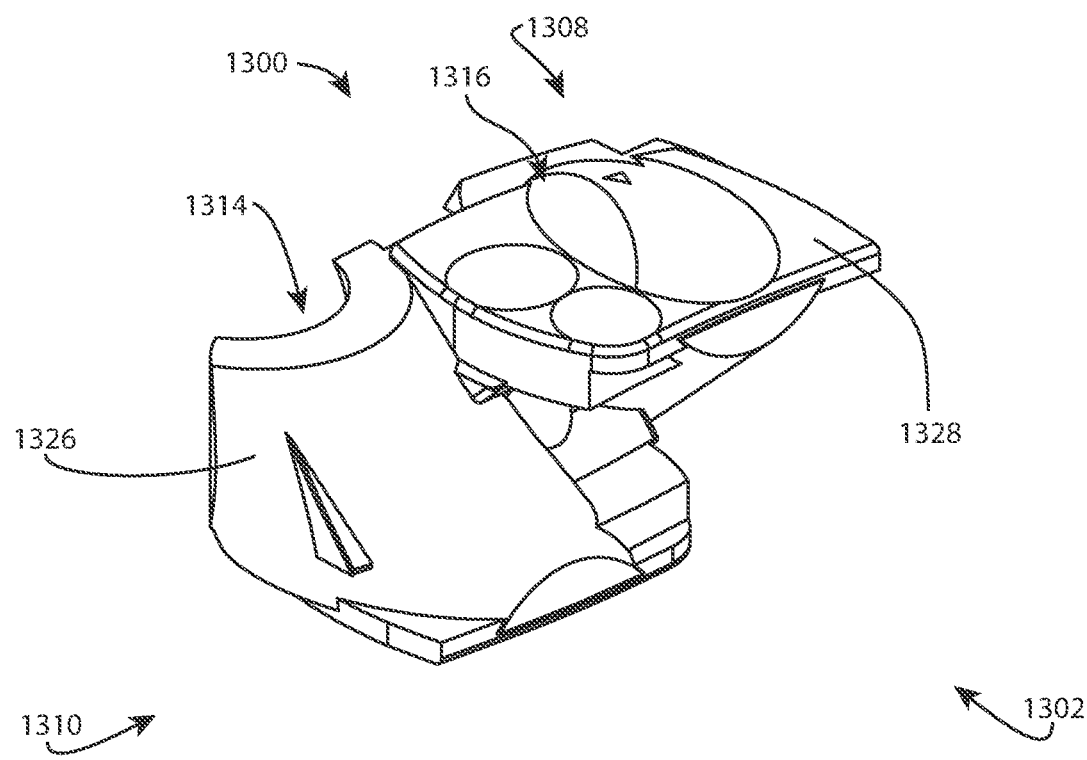
FIG. 42 is another oblique view of the porous body of FIG. 41 from a different direction.
Figure 52:
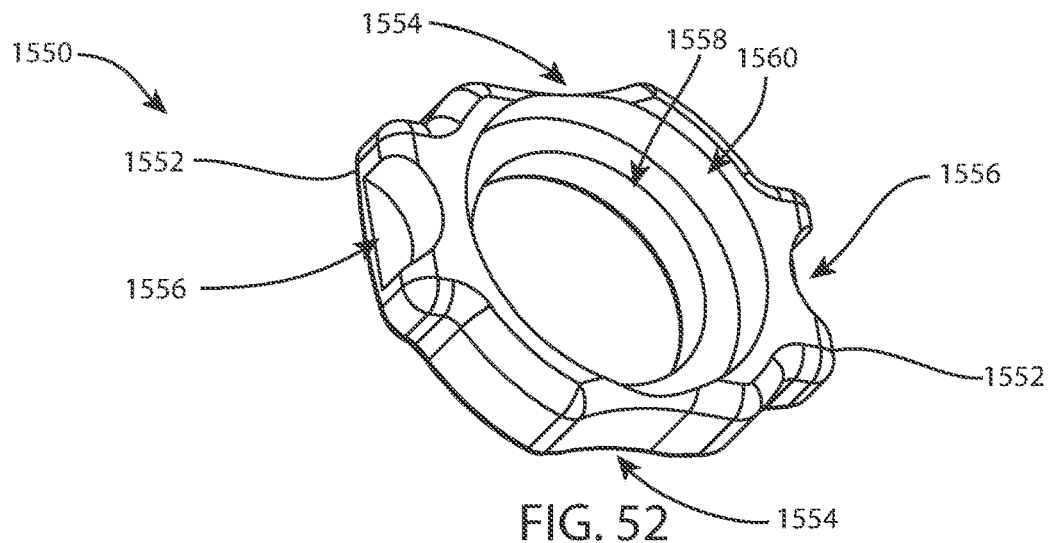
FIG. 52 is an oblique view of a collar of the intervertebral spacer of FIG. 26.
Figure 53:
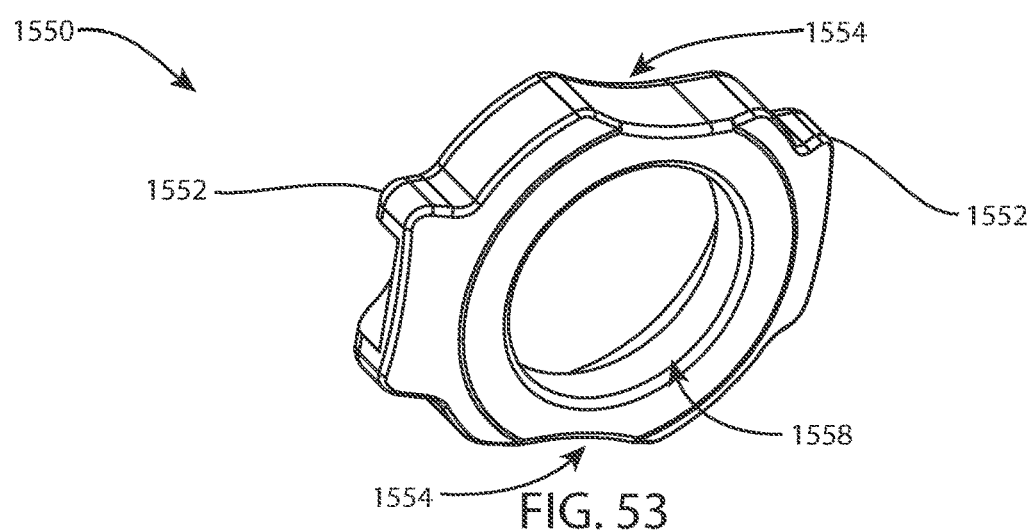
FIG. 53 is another oblique view of the collar of FIG. 52 from a different direction.

FIG. 42 is another oblique view of the porous body 1300 of FIG. 41 showing the leading side 1302, the second side 1308, and the right side 1310. The porous body 1300 includes an inferior porous structure 1328 which may be identical to the superior porous structure 1320 as shown, interchangeable, or mirror images. The first side 1306 of the porous body 1300 is a mirror image of the second side 1308 of the porous body 1308 and may be interchangeable.

FIGS. 43-48 show the structure of the porous body 1300 indicating the placement of the superior porous structure 1320 and the inferior porous structure 1328. The second side 1308 is the mirror image of the first side 1306. FIG. 48 depicts the mounding on top of the superior and inferior prominences 1322, 1324. When the solid body 1200 and the porous body 1300 are coupled together or superimposed, the porous prominences on both the first side 1306 and the second side 1308 are seated within the lobal apertures of the solid body 1200 in such a way that the mounds on top of the prominences may extend above, or outward from, the surfaces of the lobes of the solid body 1200. This extension allows the vertebral bone to contact the porous body 1300 first under compression to promote bone growth into the porous material. FIG. 48 is a cross-sectional view of FIG. 45 along section line 48-48 that shows the centralized bore 1318.

Referring to FIGS. 49-51, a helical blade 1450 has a head 1452 that includes a drive and/or insertion feature 1454 to receive torque from a screw driver or inserter tool (not shown). The drive and/or insertion feature 1454 is illustrated as an internally threaded socket for one-way torque transmission or for connection to an inserter tool. The head 1452 may also include one or more notches 1456; four notches are shown, evenly arranged around an exterior top edge of the head. Below the head 1452 is a tapered portion 1458. Below the tapered portion is a helically fluted shank 1460 or shaft that may have a tapered end 1462. Referring to FIG. 50, three helical flutes are shown, each with an associated land 1464 extending along an outer diameter of the shank 1460. The helical flute profile may form an undercut so that each flute includes a neck 1466 that is narrower than the land 1464 to enhance fixation within bone. The neck 1466 is located interior to the land 1464. The pitch of the helical flutes may be substantially equal to the length of the helically fluted shank 1460. The helical blade 1450 may be impacted into bone with a mallet or other tool, or it may be inserted by rotating it like a screw.

Referring to FIGS. 29, 32, 52, and 53, the collar 1550 may be referred to as a washer or a cam. The collar 1550 may have a non-circular outer profile, which may include a pair of tabs 1552 extending from opposite sides of the collar and/or a pair of indentations 1554 extending into opposite sides of the collar. The top surface of each tab 1552 may include a recess 1556, which may be semicircular as shown. A central through hole 1558 may extend through the collar 1550. A counterbore 1560 may be associated with the hole 1558 on the top side of the collar 1550.

Figure 32:
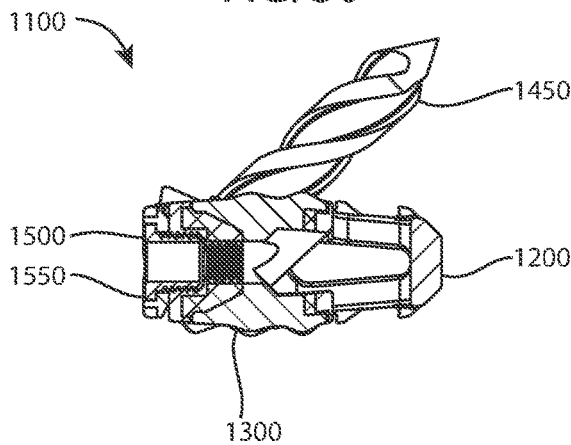
FIG. 32 is a cross-sectional view of the intervertebral spacer of FIG. 26 taken along section line 32-32 of FIG. 29.
Figure 54:
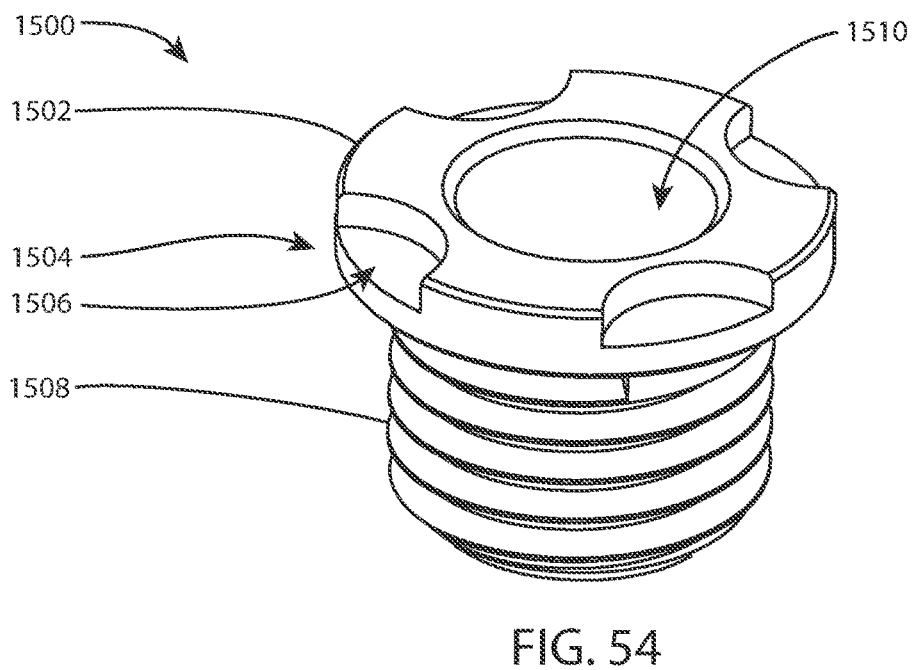
FIG. 54 is an oblique view of a bushing of the intervertebral spacer of FIG. 26.

Referring to FIGS. 32 and 54, the bushing 1500 may be referred to as a screw. The bushing 1500 has a head 1502 that may include a drive feature 1504 to receive torque from a screw driver (not shown). The drive feature 1504 may include one or more indentations 1506 in an exterior top edge of the head 1502; four semicircular indentations are shown, evenly arranged around the head. Below the head 1502 is a threaded shank 1508 or shaft which may be complementary to the internal threads of the counterbore 1246. A central longitudinal hole 1510 may extend through the bushing 1500.

The solid body 1200 and the porous body 1300 may be fabricated together at the same time via additive manufacturing technology. Thus, the disclosed solid body 1200 and porous body 1300 may be superimposed or "occupy the same space." The material of the solid body 1200 may be fully dense or non-porous, or the material may be distinctly more dense or less porous than the porous body 1300. The solid body 200 may be 80% to 100% dense. The porous body 1300 may be 80%±10% dense or 80%±5% dense. The material of the porous body 1300 may have one or more pore sizes and/or shapes which are favorable for bone ongrowth/ingrowth. The material of the porous body 1300 may have a consistent porous structure throughout, or there may be one or more gradients or abrupt changes in porous structure. The porous body 1300 may provide sufficient internal support structure to the solid body lobes so that no additional temporary support structure is required to ensure that the solid body builds according to specifications via additive manufacturing process. Preferably, the taper angles of the pedestals 1326 of the porous body 1300 may be selected to be compatible with the taper angles that a given additive manufacturing system will build without additional temporary support structure and with satisfactory finished product. Preferably, the taper angles of the pedestals 1326 of the porous body 1300 may be 45° or less. In one example, the solid body 1200 and the porous body 1300 may be fabricated together by additive manufacturing with the solid and porous bodies 1200, 1300 superimposed and oriented so that the leading side 1202 is the base on which the bodies are built or printed, in other words, the first layer of the build, and the trailing side 1204 includes the last layer of the build. In another example, the build orientation may be reversed so that the build starts with the trailing side 1204 and ends with the leading side 1202.

The centralized bore 1318 of the porous body surrounds the centralized bore 1244 of the solid body, and may optionally receive the supporting structure 1250. The right bore 1314 surrounds the right bore 1228. The left bore 1316 surrounds the left bore 1240. The superior porous structure 1320 supports the superior lobe 1224. The inferior porous structure 1328 supports the inferior lobe 1242. The porous prominences 1322, 1324 may extend outwardly through the aperture 1230 as shown. Alternatively, the solid structure of the lobes 1224, 1242 may extend outwardly past the porous structures 1320, 1328 and corresponding prominences 1322, 1324. The porous body 1300 may fill only a portion of the central cavity 1226 of the solid body, so that a portion of the cavity 1226 remains empty to receive bone graft or other therapeutic agents. Preferably, the empty portion of the cavity 1226 extends through the interconnected solid and porous bodies 1200, 1300 along a superior-inferior direction. The porous body 1300, or at least the superior and inferior porous structures 1320, 1328, may be flexible enough to permit the lobes 1224, 1242 to flex inwardly toward a central transverse plane of the implant under compressive loads applied by adjacent superior and inferior vertebrae. The central transverse plane of the implant is represented by section line 36-36 of FIG. 37 and section line 44-44 of FIG. 45. The central sagittal plane of the implant is represented by section lines 32-32 of FIG. 29, 40-40 of FIG. 37, and 48-48 of FIG. 45.

The intervertebral spacer implant system 1100 may be assembled by providing the solid body 1200 and the porous body 1300 fabricated together as a single integral part; placing the bottom side of the collar 1550 against the sunken region 1248 of the solid body 1200, optionally with the tabs 1552 extending toward the first and second sides 1206, 1208; inserting the threaded shank 1508 of the bushing 1500 through the hole 1558 and threading it into the internal threads of the counterbore 1246, optionally leaving the threaded interconnection loose or less than fully tight; inserting the helically fluted shank 1460 of the helical blade 1450 into the right bore 1228 so that the head 1452 is at or near the trailing side 1204 and the helically fluted shank 1460 protrudes from the first side 1206; inserting the threaded shank 410 of the bone screw 404 into the left bore 1240 so that the head 406 is at or near the trailing side 1204 and the threaded shank 410 protrudes from the second side 1208; rotating the collar 1550 so that the tabs 1552 extend toward the right and left sides 1210, 1212, optionally with a portion of one tab 1552 received in a notch 1456; and fully tightening the bushing 1500 to lock the collar 1550 in position to prevent the helical blade 1450 and/or the bone screw 404 from backing out of the right and left bores 1228, 1240, respectively. Optionally, the bone screw 404 may be inserted into the right bore 1228 and the helical blade 1450 may be inserted into the left bore 1240. Optionally, bone screws 402, 404 or two helical blades 1450 may be inserted into the right and left bores 1228, 1240.

A method of implanting the intervertebral spacer implant system 1100 may include some or all of the following steps in any order: creating a surgical access to an operative site, removing a disc from between adjacent superior and inferior vertebrae, inserting the leading side of the solid/porous spacer 1200, 1300 along a trailing-leading direction into the prepared disc space, optionally drilling for the bone screw(s) 404 and/or helical blade(s) 1450, inserting the bone anchors through the bores 1228, 1240 and into the vertebral bodies, and after the bone anchors are fully inserted, rotating the collar 1550 so that the tabs 1552 cover at least a portion of each bone anchor head, including optionally engaging a notch 1456, tightening the bushing 1500 in the counterbore 1246, and closing the surgical access.

Referring to FIGS. 55A-57B, a porous body 1600 is shown to illustrate an example porous structure. The porous structure illustrated by porous body 1600 may be included in porous bodies 300, 1300. FIG. 55A is a top view of the porous body 1600 and FIG. 55B is an enlarged detail view of a portion of the porous body 1600 of FIG. 55A, showing that in the top view, the porous structure is formed by interconnecting struts 1614 which define hexagonal pores 1616 that extend straight through the porous body 1600. Similarly, FIG. 57A is a side view of the porous body 1600 and FIG. 57B is an enlarged detail view of a portion of the porous body 1600 of FIG. 57A, showing that in the side view, the porous structure is formed by interconnecting struts 1618 which define hexagonal pores 1620 that extend straight through the porous body 1600. The size, shape, and orientation of the struts 1614 and pores 1616 shown in FIGS. 55A-B may be the same as in FIGS. 57A-B, or different as shown. FIG. 56A is a front view of the porous body 1600 and FIG. 56B is an enlarged detail view of a portion of the porous body 1600 of FIG. 56A, showing that in the front view, the porous structure is formed by interconnecting struts 1622 which define rectangular (or square) pores 1624 that extend straight through the porous body 1600. The rectangular pores 1624 may have the same cross-sectional area as the hexagonal pores 1616, 1620, or different as shown. FIGS. 56A-B also show that the porous structure may be formed by interconnecting perpendicular layers corresponding to FIGS. 55A-B and 57A-B. It will be appreciated that the porous structure may include additional void space besides the hexagonal and rectangular pores 1616, 1620, 1624.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. An intervertebral implant system comprising:
an intervertebral spacer comprising a solid body and a porous body integrally formed together as a single part, wherein the intervertebral spacer comprises a leading side, an opposite trailing side, a first side, an opposite second side, a right side, an opposite left side, a perimeter wall, a first lobe, and a bone anchor hole; wherein:
the perimeter wall extends around the leading, trailing, right, and left sides between the first and second sides;
the first lobe extends from the perimeter wall across a portion of the first side toward a central region of the first side;
the first lobe is elevated outwardly relative to the perimeter wall at the first side;
the solid body comprises a first solid portion of the first lobe and the porous body comprises a first porous portion of the first lobe;
the first porous portion of the first lobe is elevated outwardly relative to the first solid portion of the first lobe and the perimeter wall at the first side; and
the bone anchor hole extends through the first lobe so that the first lobe surrounds the bone anchor hole; and
a bone anchor configured to be received in the bone anchor hole so that a portion of the bone anchor protrudes outwardly from the first side.

2. The system of claim 1, wherein the solid body comprises the perimeter wall, wherein the perimeter wall surrounds the porous body and abuts a perimeter portion of the porous body.

3. The system of claim 2, wherein the porous body supports at least a portion of the perimeter wall during fabrication of the intervertebral spacer.

4. The system of claim 1, wherein the bone anchor hole extends obliquely through the perimeter wall and the first lobe.

5. The system of claim 4, wherein the solid body comprises a wall extending obliquely between the perimeter wall and the first lobe, and surrounding the bone anchor hole.

6. The system of claim 1, comprising:
a locking mechanism;
wherein the bone anchor comprises a head, wherein the head comprises a notch;
wherein when the bone anchor is received in the bone anchor hole, the notch engages the locking mechanism to prevent the bone anchor from backing out of the bone anchor hole.

7. An intervertebral implant system comprising:
an intervertebral spacer comprising a leading side, a trailing side opposite the leading side, a first bone-facing side, a second bone-facing side opposite the first bone-facing side, a right side, a left side opposite the right side, a perimeter wall, a first lobe, and a bone anchor hole;
wherein:
the perimeter wall extends around the leading side, trailing side, right side, and left side between the first and second bone-facing sides;
the first lobe extends from the perimeter wall across a portion of the first bone-facing side toward a central region of the first bone-facing side;
the first lobe is elevated outwardly relative to the perimeter wall at the first bone-facing side;
the intervertebral spacer comprises a solid body and a porous body integrally formed together as a single part, wherein the solid body comprises a first solid portion of the first lobe and the porous body comprises a first porous portion of the first lobe;
the first porous portion of the first lobe is elevated outwardly relative to the first solid portion of the first lobe and the perimeter wall at the first bone-facing side; and
the bone anchor hole extends obliquely through the perimeter wall and the first lobe so that the first lobe surrounds the bone anchor hole; and
a bone anchor configured to be received in the bone anchor hole so that a portion of the bone anchor protrudes outwardly from the first bone-facing side.

8. The system of claim 7, wherein the intervertebral spacer comprises a solid body and a porous body integrally formed together as a single part, wherein the solid body comprises the perimeter wall, wherein the perimeter wall surrounds the porous body and abuts a perimeter portion of the porous body.

9. The system of claim 8, wherein the porous body supports at least a portion of the perimeter wall during fabrication of the intervertebral spacer.

10. The system of claim 7, wherein the bone anchor hole is surrounded by a wall that extends the full length of the bone anchor hole between the perimeter wall and the first lobe.

11. The system of claim 10, wherein the intervertebral spacer comprises a solid body and a porous body integrally formed together as a single part, wherein the solid body comprises the wall that surrounds the bone anchor hole.

12. The system of claim 7, comprising:
a locking mechanism;
wherein the bone anchor comprises a head, wherein the head comprises a notch;
wherein when the bone anchor is received in the bone anchor hole, the notch engages the locking mechanism to prevent the bone anchor from backing out of the bone anchor hole.

* * * * *